United States Patent
Jaiser et al.

(10) Patent No.: US 12,329,840 B2
(45) Date of Patent: Jun. 17, 2025

(54) AGENT FOR DYEING KERATIN MATERIAL, CONTAINING AT LEAST TWO ORGANOSILICON COMPOUNDS THAT ARE DIFFERENT FROM EACH OTHER, AT LEAST ONE PIGMENT AND AT LEAST ONE LIQUID FATTY COMPONENT AND/OR A SOLVENT

(71) Applicant: HENKEL AG & CO. KGAA, Duesseldorf (DE)

(72) Inventors: Phillip Jaiser, Langenfeld (DE); Torsten Lechner, Langenfeld (DE); Juergen Schoepgens, Schwalmtal (DE); Marc Nowottny, Moenchengladbach (DE); Carsten Mathiaszyk, Essen (DE); Andreas Walter, Ratingen (DE); Carolin Kruppa, Hilden (DE); Avni Tairi, Duisburg (DE)

(73) Assignee: Henkel AG & Co. KGaA, Düesseldorf (DE)

( * ) Notice: Subject to any disclaimer, the term of this patent is extended or adjusted under 35 U.S.C. 154(b) by 0 days.

(21) Appl. No.: 18/272,368

(22) PCT Filed: Jan. 12, 2022

(86) PCT No.: PCT/EP2022/050557
§ 371 (c)(1),
(2) Date: Jul. 14, 2023

(87) PCT Pub. No.: WO2022/167185
PCT Pub. Date: Aug. 11, 2022

(65) Prior Publication Data
US 2024/0099953 A1  Mar. 28, 2024

(30) Foreign Application Priority Data
Feb. 5, 2021 (DE) .................. 10 2021 201 097.0

(51) Int. Cl.
*A61Q 5/10* (2006.01)
*A61K 8/58* (2006.01)
*A61K 8/891* (2006.01)

(52) U.S. Cl.
CPC ............. *A61K 8/585* (2013.01); *A61K 8/891* (2013.01); *A61Q 5/10* (2013.01); *A61K 2800/95* (2013.01)

(58) Field of Classification Search
CPC .... A61K 8/585; A61K 8/891; A61K 2800/95; A61K 8/34; A61K 8/345; A61K 2800/43; A61Q 5/10; A61Q 5/065
USPC .......................................................... 8/405
See application file for complete search history.

(56) References Cited

U.S. PATENT DOCUMENTS

| | | | |
|---|---|---|---|
| 2010/0083446 A1* | 4/2010 | Brun | ....................... A61K 8/891 8/405 |
| 2022/0202682 A1 | 6/2022 | Weser et al. | |
| 2022/0218582 A1 | 7/2022 | Krohn et al. | |
| 2022/0249345 A1 | 8/2022 | Lechner et al. | |
| 2022/0354765 A1 | 11/2022 | Krohn et al. | |
| 2023/0149278 A1 | 5/2023 | Hippe et al. | |

FOREIGN PATENT DOCUMENTS

| | | | | |
|---|---|---|---|---|
| DE | 102019204802 A1 | 10/2020 | | |
| DE | 102019206912 A1 | 11/2020 | | |
| DE | 102019206915 A1 | 11/2020 | | |
| DE | 102019207062 A1 | 11/2020 | | |
| EP | 2168633 B1 | 3/2016 | | |
| FR | 3099990 A1 | 2/2021 | | |
| WO | WO 2020200544 A1 * | 10/2020 | ............... | A61Q 5/10 |
| WO | 2021180369 A1 | 9/2021 | | |
| WO | 2021204441 A1 | 10/2021 | | |

* cited by examiner

Primary Examiner — Eisa B Elhilo
(74) Attorney, Agent, or Firm — Blank Rome LLP

(57) ABSTRACT

An agent for dyeing keratin material, such as human hair, may include at least two organosilicon compounds different from each other. Each organosilicon compound may be independently selected from silanes with one, two, or three silicon atoms, and the organosilicon compound may include one or more hydroxyl groups and/or hydrolyzable groups per molecule. The agent may include at least one pigment, and at least one fatty component that is liquid at 20° C. and/or an organic solvent. The agent may be used for dyeing keratin material.

19 Claims, No Drawings

AGENT FOR DYEING KERATIN MATERIAL, CONTAINING AT LEAST TWO ORGANOSILICON COMPOUNDS THAT ARE DIFFERENT FROM EACH OTHER, AT LEAST ONE PIGMENT AND AT LEAST ONE LIQUID FATTY COMPONENT AND/OR A SOLVENT

CROSS-REFERENCE TO RELATED APPLICATIONS

The present application is a national stage entry according to 35 U.S.C. § 371 of PCT application No.: PCT/EP2022/050557 filed on Jan. 12, 2022; which claims priority to German patent application 10 2021 201 097.0 filed on Feb. 5, 2021; all of which are incorporated herein by reference in their entirety and for all purposes.

TECHNICAL FIELD

The present application relates to an agent for dyeing keratin material, in particular human hair, which contains at least two different organosilicon compounds, at least one pigment, and at least one liquid fatty component and/or a solvent.

This application also relates to a method for dyeing keratin material, in particular human hair, in which the hair is first moistened and then the agent of the first object of the invention is applied to the moistened hair.

BACKGROUND

Changing the shape and color of keratin material, in particular hair, represents an important field of modern cosmetics. To change the hair color, a person skilled in the art is familiar with a variety of coloring systems depending on the coloring requirements. Oxidation dyes are typically used for permanent, intense dyeing with good fastness properties and good gray coverage. Such coloring agents contain oxidation dye precursors, so-called developer components and coupler components, which together form the actual dyes under the influence of oxidizing agents, such as, for example, hydrogen peroxide. Oxidation dyes are characterized by very long-lasting color results.

When using direct dyes, dyes which are already formed diffuse out of the coloring agent into the hair fiber. In comparison with oxidative hair coloring, the colors obtained with direct dyes have a lower durability and a more rapid washing out. Colors with direct dyes usually remain on the hair for a period of between 5 and 20 hair washes.

The use of color pigments for brief changes in color on the hair and/or the skin is known. Color pigments are generally understood to mean insoluble coloring substances. These are present undissolved in the form of small particles in the dyeing formulation and are only deposited from the outside onto the hair fibers and/or the skin surface. They can therefore generally be removed again without leaving residue by washing a few times with surfactant-containing cleaning agents. Various products of this type by the name of hair mascara are available on the market.

If the user desires particularly long-lasting colors, the use of oxidative coloring agents has hitherto been the only option. However, despite multiple optimization attempts, an unpleasant ammonia odor or amine odor cannot be completely avoided in oxidative hair dyeing. The hair damage that remains associated with the use of the oxidative coloring agents also has a disadvantageous effect on the hair of the user. The search for alternative, high-performance dyeing methods is therefore an ongoing challenge.

EP 2168633 B1 deals with the task of producing long-lasting hair coloring using pigments. The document teaches that, when using a combination of pigment, organosilicon compound, hydrophobic polymer and a solvent, colors can be produced on hair which are particularly resistant to shampoos. 3-aminopropyl triethoxysilane was, for example, used as the organosilicon compound.

In the dyeing methods of EP 2168633 B1, organosilicon compounds from the group of silanes are used, wherein the molecular structure of these silanes comprises at least one hydroxy group and/or hydrolyzable group. Owing to the presence of the hydroxyl groups or hydrolyzable groups, the silanes are reactive substances which hydrolyze, or oligomerize, or polymerize in the presence of water. The oligomerization or polymerization of the silanes initiated by the presence of the water ultimately leads, when applied to the keratin material, to the formation of a film which fixes the dyeing compounds and thereby produces very long-lasting colors.

Upon more closely examining the dyeing methods disclosed in EP 2168633 B1 it has been found, however, that the colors produced on the hair with these agents or methods are still in need of improvement. In particular, the abrasion of these colors from the hair must still be optimized, and also the durability, in particular the wash fastness of these colors, requires further improvement.

The object of the present invention is that of providing a dyeing system which has fastness properties comparable to oxidative dyeing. In particular, the wash fastness and rub fastness properties should be outstanding, but the use of the oxidation dye precursors normally used for this purpose should be avoided. A technique has been sought that makes it possible to fix the pigments known from the prior art, or fix them in an extremely durable manner, on the hair. The production of the coloring agents should be cost-effective, and the agents themselves should have very good storage stability. When the agents are used in a dyeing method, good color results should be achievable independent of the prevailing conditions during production and application (such as, for example, air humidity and temperature). In addition, application should be possible in the most uncomplicated way possible so that the user can quickly and specifically apply the coloring agent to the hair without having to mix and homogenize different formulations beforehand.

SUMMARY

Surprisingly, it has been found that the aforementioned object can be achieved in an excellent manner when keratin materials, in particular hair, are colored with an agent which contains at least two hydrolyzable organosilicon compounds (a) that are different from each other, at least one pigment (b), as well as at least one fatty component that is liquid at 20° C. and/or an organic solvent (c).

The present invention first relates to an agent for dyeing keratin material, in particular human hair, containing:
 (a) at least two different organosilicon compounds, wherein each organosilicon compound is selected independently of the other from the group of silanes with one, two or three silicon atoms, wherein the organosilicon compound comprises one or more hydroxyl groups and/or hydrolyzable groups per molecule,
 (b) at least one pigment, and
 (c) at least one fatty component that is liquid at 20° C. and/or an organic solvent.

DETAILED DESCRIPTION

Keratin Material

Keratin material is understood to mean hair, skin, and nails (such as, for example, fingernails and/or toenails). Furthermore, wool, furs and feathers also fall under the definition of the keratin material.

Keratin material is preferably understood to be human hair, human skin and human nails, in particular fingernails and toenails. Keratin material is very particularly preferably understood to mean human hair.

Agent for Dyeing Keratin Material

The agent according to the invention for dyeing keratin material contains the essential components (a), (b) and (c), with the coloring effect being achieved by the pigments or color pigments (b) containing the agent.

In the context of this invention, the term "agent for dyeing" is used for coloring the keratin material, in particular the hair, brought about by use of pigments. In this dyeing, the aforementioned pigments are deposited in a particularly homogeneous and smooth film on the surface of the keratin material. The film forms in situ by oligomerization or polymerization of the organosilicon compounds, as well as by the interaction of the organosilicon compound with the pigment or pigments.

The agent according to the invention can be formulated as a concentrate so that the components (a), (b) and (c) represent the quantitative main components of the agent. In this context, the main component refers to an ingredient of which the amount used exceeds that of all other ingredients.

In another embodiment, the agent can also contain the components (a), (b) and (c) in a cosmetic carrier which can be hydrous, low-water or also anhydrous. In addition, the cosmetic carrier can be liquid, gel, cream, powder or solid (for example in the form of a tablet or a pellet). For the purpose of hair coloring, such carriers are for example creams, emulsions, gels or also surfactant-containing foaming solutions, such as shampoos, foam aerosols, foam formulations or other preparations, in particular concentrates, which are suitable for application to keratin material or hair.

At Least Two Different Organosilicon Compounds (a)

The agent (a) contains at least two different organosilicon compounds as the first substance class essential to the invention. Each of these organosilicon compounds is selected from silanes with one, two or three silicon atoms, wherein the organosilicon compound comprises one or more hydroxyl groups and/or hydrolyzable groups per molecule.

If the agent according to the invention contains two different silanes, each silane is selected independently of the other silane from the group of silanes with one, two or three silicon atoms. Each of the two selected organosilicon compounds comprises one or more hydroxyl groups and/or hydrolyzable groups per molecule.

If the agent according to the invention contains three different silanes, each of the three silanes is selected independently of the other two silanes from the group of silanes with one, two or three silicon atoms. Each of the three silanes comprises one or more hydroxyl groups and/or hydrolyzable groups per molecule.

The organosilicon compounds or organic silanes in the agent (a) are reactive compounds.

Organosilicon compounds, which are alternatively also referred to as organic silicon compounds, are compounds which either have a direct silicon-carbon bond (Si—C), or in which the carbon is linked to the silicon atom via an oxygen, nitrogen or sulfur atom. The organosilicon compounds according to the invention are compounds which contain one to three silicon atoms. The organosilicon compounds particularly preferably contain one or two silicon atoms.

According to the IUPAC rules, the term silane represents a substance group of chemical compounds based on a silicon backbone and hydrogen. In the case of organic silanes, the hydrogen atoms are completely or partially replaced by organic groups such as (substituted) alkyl groups and/or alkoxy groups. Some of the hydrogen atoms can also be replaced by hydroxyl groups in the organic silanes.

The agent (a) contains at least two organosilicon compounds that are different from each other, each selected from silanes with one, two or three silicon atoms, wherein each organosilicon compound comprises one or more hydroxyl groups or hydrolyzable groups per molecule. Organosilicon compounds that are different from each other are understood to mean two substances of which the molecular structure is different from each other.

In the context of a very particularly preferred embodiment, an agent according to the invention is characterized in that it contains at least one first organosilicon compound (a1) selected from silanes with one, two or three silicon atoms, wherein the organosilicon compound also comprises one or more basic chemical functions and one or more hydroxyl groups or hydrolyzable groups per molecule.

This basic group may be, for example, an amino group, an alkylamino group or a dialkylamino group which is preferably connected to a silicon atom via a linker. Preferably, the basic group is an amino group, a $C_1$-$C_6$ alkylamino group or a $Di(C_1$-$C_6)$ alkylamino group.

The hydrolyzable group(s) are preferably a $C_1$-$C_6$ alkoxy group, in particular an ethoxy group or a methoxy group. It is preferred if the hydrolyzable group is present directly bound to the silicon atom. If, for example, the hydrolyzable group is an ethoxy group, the organosilicon compound preferably contains a structural unit R'R"R'"Si—O—CH2-CH3. The R', R" and R'" functional groups here represent the three remaining free valencies of the silicon atom.

A very particularly preferred agent according to the invention is characterized in that it contains at least one first organosilicon compound (a1) selected from silanes with one, two or three silicon atoms, wherein the organosilicon compound preferably comprises one or more basic chemical functions and one or more hydroxyl groups or hydrolyzable groups per molecule.

Excellent results were obtained when the agent according to the invention contained at least one first organosilicon compound (a1) of formula (I) and/or (II).

The compounds of formulas (I) and (II) are organosilicon compounds selected from silanes with one, two or three silicon atoms, wherein the organosilicon compound comprises one or more hydroxyl groups and/or hydrolyzable groups per molecule.

In another particularly preferred embodiment, an agent according to the invention is characterized in that it contains at least one first organosilicon compound (a1) of formula (I) and/or formula (II):

$$R_1R_2N\text{-}L\text{-}Si(OR_3)_a(R_4)_b \qquad (I),$$

where
- $R_1$ and $R_2$ represent, independently of one another, a hydrogen atom or a $C_1$-$C_6$ alkyl group,
- L represents a linear or branched divalent $C_1$-$C_{20}$ alkylene group,
- $R_3$ and $R_4$ represent, independently of one another, a $C_1$-$C_6$ alkyl group, a represents an integer from 1 to 3, and b represents the integer 3−a, and where, in the organosilicon compound of formula (II),

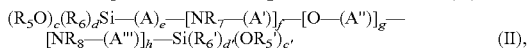
(II),

R5, R5', R5'', R6, R6' and R6'' represent, independently of one another, a $C_1$-$C_6$ alkyl group, A, A', A'', A''' and A'''' represent, independently of one another, a linear or branched, divalent $C_1$-$C_{20}$ alkylene group, $R_7$ and $R_8$ represent, independently of one another, a hydrogen atom, a $C_1$-$C_6$ alkyl group, a hydroxy $C_1$-$C_6$ alkyl group, a $C_2$-$C_6$ alkenyl group, an amino $C_1$-$C_6$ alkyl group or a group of formula (III), —(A'''')—Si($R_6$'')$_{d''}$(O$R_5$'')$_{c''}$  (III), c represents an integer from 1 to 3, d represents the integer 3−c, c' represents an integer from 1 to 3, d' represents the integer 3−c', c'' represents an integer from 1 to 3, d'' represents the integer 3−c'', e represents 0 or 1, f represents 0 or 1, g represents 0 or 1, h represents 0 or 1, with the proviso that at least one of the functional groups from e, f, g and h is different from 0.

The substituents $R_1$, $R_2$, $R_3$, $R_4$, $R_5$, $R_5'$, $R_5''$, $R_6$, $R_6'$, $R_6''$, $R_7$, $R_8$, L, A, A', A'', A''' and A'''' in the compounds of formula (I) and (II) are explained by way of example below:

Examples of a $C_1$-$C_6$ alkyl group are the groups methyl, ethyl, propyl, isopropyl, n-butyl, s-butyl and t-butyl, n-pentyl and n-hexyl. Propyl, ethyl and methyl are preferred alkyl functional groups. Examples of a $C_2$-$C_6$ alkenyl group are vinyl, allyl, but-2-enyl, but-3-enyl and isobutenyl; preferred $C_2$-$C_6$ alkenyl functional groups are vinyl and allyl. Preferred examples of a hydroxy-$C_1$-$C_6$ alkyl group are a hydroxymethyl, a 2-hydroxyethyl, a 2-hydroxypropyl, a 3-hydroxypropyl, a 4-hydroxybutyl group, a 5-hydroxypentyl and a 6-hydroxyhexyl group; a 2-hydroxyethyl group is particularly preferred. Examples of an amino-$C_1$-$C_6$ alkyl group are the aminomethyl group, the 2-aminoethyl group, and the 3-aminopropyl group. The 2-aminoethyl group is particularly preferred. Examples of a linear divalent $C_1$-$C_{20}$ alkylene group are, for example, the methylene group (—CH$_2$—), the ethylene group (—CH—CH$_2$—), the propylene group (—CH$_2$—CH$_2$—CH$_2$—) and the butylene group (CH$_2$—CH$_2$—CH$_2$—CH$_2$—). The propylene group (—CH$_2$—CH$_2$—CH$_2$—) is particularly preferred. Starting at a chain length of 3 C atoms, divalent alkylene groups may also be branched. Examples of branched, divalent $C_3$-$C_{20}$ alkylene groups are (—CH$_2$—CH(CH$_3$)—) and (—CH$_2$—CH(CH$_3$)—CH$_2$—).

In the organosilicon compound of formula (I)

(I), the functional groups $R_1$ and $R_2$ represent, independently of one another, a hydrogen atom or a $C_1$-$C_6$ alkyl group. Most preferably, the functional groups $R_1$ and $R_2$ both represent a hydrogen atom.

In the middle part of the organosilicon compound is the structural unit or linker -L- which represents a linear or branched divalent $C_1$-$C_{20}$ alkylene group.

Preferably, -L- represents a linear, divalent $C_1$-$C_{20}$ alkylene group. More preferably, -L- represents a linear divalent $C_1$-$C_6$ alkylene group. Particularly preferably, -L- represents a methylene group (—CH$_2$—), an ethylene group (—CH$_2$—CH$_2$—), a propylene group (—CH$_2$—CH$_2$—CH$_2$—) or a butylene group (—CH$_2$—CH$_2$—CH$_2$—CH$_2$—). Most preferably, L represents a propylene group (—CH$_2$—CH$_2$—CH$_2$—).

The organosilicon compounds of formula (I) according to the invention $R_1R_2N$-L-Si(O$R_3$)$_a$(R$_4$)$_b$  (I), each bear, on one end, the silicon-containing group —Si(O$R_3$)$_a$(R$_4$)$_b$.

In the terminal structural unit —Si(O$R_3$)$_a$(R$_4$)$_b$, the functional group $R_3$ represents a hydrogen atom or a $C_1$-$C_6$ alkyl group, and the functional group $R_4$ represents a $C_1$-$C_6$ alkyl group. Particularly preferably, $R_3$ and $R_4$ represent, independently of one another, a methyl group or an ethyl group.

In this case, a represents an integer from 1 to 3, and b represents the integer 3−a. If a represents the number 3, then b is equal to 0. If a represents the number 2, then b is equal to 1. If a represents the number 1, then b is equal to 2.

Colors with the best wash fastness were obtained when the agent according to the invention contained at least one first organosilicon compound (a1) of formula (I), where the functional groups $R_3$ and $R_4$ represent, independently of one another, a methyl group or an ethyl group.

Furthermore, colors having the best wash fastness were obtained when the agent according to the invention contained at least one first organosilicon compound (a1) of formula (I) where the functional group a represents the number 3. In this case, the functional group b represents the number 0.

In another preferred embodiment, an agent according to the invention is characterized in that it contains at least one first organosilicon compound (a1) of formula (I), where $R_3$ and $R_4$ represent, independently of one another, a methyl group or an ethyl group, and a represents the number 3, and b represents the number 0.

In another preferred embodiment, an agent according to the invention is characterized in that it contains at least one first organosilicon compound (a1) of formula (I),

(I), where $R_1$ and $R_2$ both represent a hydrogen atom, and

L represents a linear, divalent $C_1$-$C_6$ alkylene group, preferably a propylene group (—CH$_2$—CH$_2$—CH$_2$—) or an ethylene group (—CH$_2$—CH$_2$—), $R_3$ and $R_4$ represent, independently of one another, a methyl group or an ethyl group, and a represents the number 3, and b represents the number 0.

To achieve the object according to the invention, particularly well-suited organosilicon compounds of formula (I) are:

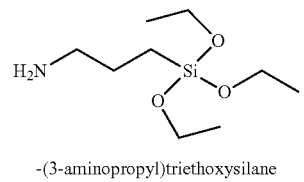

-(3-aminopropyl)triethoxysilane

-continued

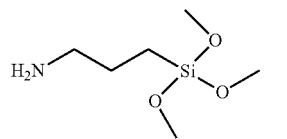
-(3-aminopropyl)trimethoxysilane

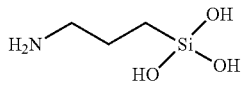
-1-(3-aminopropyl)silanetriol

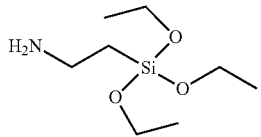
-(2-aminoethyl)triethoxysilane

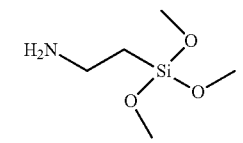
-(2-aminoethyl)trimethoxysilane

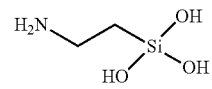
-1-(2-aminoethyl)silanetriol

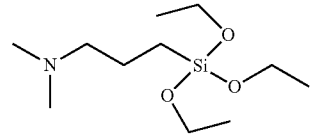
-(3-dimethylaminopropyl)triethoxysilane

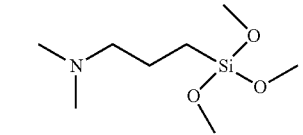
-(3-dimethylaminopropyl)trimethoxysilane

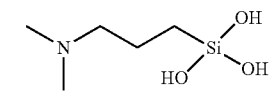
1-(3-dimethylaminopropyl)silanetriol

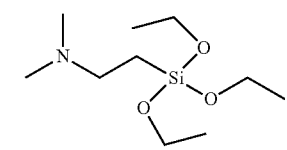
-(2-dimethylaminoethyl)triethoxysilane

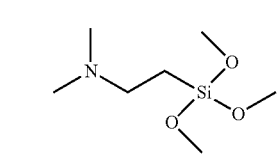
-(2-dimethylaminoethyl)trimethoxysilane, and/or

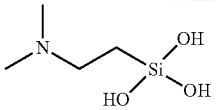
1-(2-dimethylaminoethyl)silanetriol

In another preferred embodiment, an agent according to the invention is characterized in that it contains at least one first organosilicon compound (a1) of formula (I) selected from the group consisting of:
(3-aminopropyl)triethoxysilane
(3-aminopropyl)trimethoxysilane
1-(3-aminopropyl)silanetriol
(2-aminoethyl)triethoxysilane
(2-aminoethyl)trimethoxysilane
1-(2-aminoethyl)silanetriol
(3-dimethylaminopropyl)triethoxysilane
(3-dimethylaminopropyl)trimethoxysilane
1-(3-dimethylaminopropyl)silanetriol
(2-dimethylaminoethyl)triethoxysilane
(2-dimethylaminoethyl)trimethoxysilane, and/or
1-(2-dimethylaminoethyl)silanetriol.

In another very particularly preferred embodiment, an agent according to the invention is characterized in that it contains at least one first organosilicon compound (a1) of formula (I) selected from the group consisting of:
(3-aminopropyl)trimethoxysilane
(3-aminopropyl)triethoxysilane
(2-aminoethyl)trimethoxysilane
(2-aminoethyl)triethoxysilane
(3-dimethylaminopropyl)trimethoxysilane
(3-dimethylaminopropyl)triethoxysilane
(2-dimethylaminoethyl)trimethoxysilane, and/or
(2-dimethylaminoethyl)triethoxysilane.

The aforementioned organosilicon compounds of formula (I) are commercially available. (3-aminopropyl)trimethoxysilane can be purchased from Sigma-Aldrich, for example. (3-aminopropyl)triethoxysilane is also commercially available from Sigma-Aldrich.

In the context of another embodiment, the agent according to the invention contains at least one organosilicon compound of formula (II):

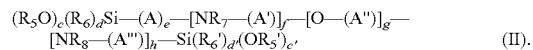

$$(R_5O)_c(R_6)_d Si\text{—}(A)_e\text{—}[NR_7\text{—}(A')]_f\text{—}[O\text{—}(A'')]_g\text{—}[NR_8\text{—}(A''')]_h\text{—}Si(R_6')_{d'}(OR_5')_{c'} \quad \text{(II)}.$$

The organosilicon compounds of formula (II) according to the invention each bear the silicon-containing groups $(R_5O)_c(R_6)_d Si\text{—}$ and $\text{—}Si(R_6')_{d'}(OR_5')_{c'}$ at their two ends.

The groups $(A)_e\text{-}$, $\text{—}[NR_7\text{—}(A')]_f\text{-}$, $\text{—}[O\text{—}(A'')]_g\text{-}$ and $\text{—}[NR_8\text{—}(A''')]_h\text{-}$ are in the middle part of the molecule of formula (II). In this case, each of the functional groups e, f, g and h can independently represent the number 0 or 1, with the proviso that at least one of the functional groups e, f, g and h is different from 0. In other words, an organosilicon compound of formula (II) according to the invention contains at least one grouping from the group consisting of $\text{—}(A)\text{—}$, $\text{—}[NR_7\text{—}(A')]\text{-}$, $\text{—}[O\text{—}(A'')]\text{-}$ and $\text{—}[NR_8\text{—}(A'\text{-})]\text{-}$.

In the two terminal structural units $(R_5O)_c(R_6)_d Si\text{—}$ and $\text{—}Si(R_6')_{d'}(OR_5')_{c'}$, the functional groups R5, R5' and R5" represent, independently of one another, a hydrogen atom or a $C_1\text{-}C_6$ alkyl group. The functional groups R6, R6' and R6" represent, independently of one another, a $C_1\text{-}C_6$ alkyl group.

In this case, c represents an integer from 1 to 3, and d represents the integer 3−c. If c represents the number 3, then d is equal to 0. If c represents the number 2, then d is equal to 1. If c represents the number 1, then d is equal to 2.

Similarly, c' represents an integer of 1 to 3, and d' represents the integer 3−c'. If c' represents the number 3, then d' is equal to 0. If c' represents the number 2, then d' is equal to 1. If c' represents the number 1, then d' is equal to 2.

Colors with the best wash fastness were obtained when the functional groups c and c' both represented the number 3. In this case, d and d' both represent the number 0.

In another preferred embodiment, an agent according to the invention is characterized in that it contains at least one first organosilicon compound (a1) of formula (II),

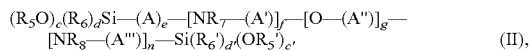

(II), where

R$_1$ and R$_4$ represent, independently of each other, a methyl group or an ethyl group, c and c' both represent the number 3, and d and d' both represent the number 0.

If c and c' both represent the number 3 and d and d' both represent the number 0, the inventive organosilicon compound of formula (IIa) corresponds to:

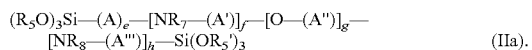

(IIa).

The functional groups e, f, g and h can independently represent the number 0 or 1, where at least one functional group of e, f, g and h is different from zero. The abbreviations e, f, g and h therefore define which of the groupings —(A)$_e$-, —[NR$_7$—(A')]$_f$-, —[O—(A'')]$_g$- and —[NR$_8$—(A''')]$_h$- are located in the middle part of the organosilicon compound of formula (II).

In this context, the presence of certain groupings has proven to be particularly advantageous with regard to increasing wash fastness. Particularly good results were obtained when at least two of the functional groups e, f, g and h represented the number 1. Most preferably, e and f both represent the number 1. Furthermore, g and h very particularly preferably both represent the number 0.

If e and f both represent the number 1, and g and h both represent the number 0, the organosilicon compound according to the invention corresponds to formula (IIb):

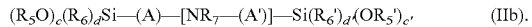

(IIb).

The functional groups A, A', A'', A''' and A'''' represent, independently of one another, a linear or branched divalent C$_1$-C$_{20}$ alkylene group. A, A', A'', A''' and A'''' preferably represent, independently of one another, a linear or branched divalent C$_1$-C$_{20}$ alkylene group. More preferably, the functional groups A, A', A'', A''' and A'''' represent, independently of one another, a linear divalent C$_1$-C$_6$ alkylene group. Particularly preferably, the functional groups A, A', A'', A''' and A'''' represent, independently of one another, a methylene group (—CH$_2$—), an ethylene group (—CH$_2$—CH$_2$—), a propylene group (—CH$_2$—CH$_2$—CH$_2$—) or a butylene group (—CH$_2$—CH$_2$—CH$_2$—CH$_2$—). Very particularly preferably, the functional groups A, A', A'', A''' and A'''' represent a propylene group (—CH$_2$—CH$_2$—CH$_2$—).

If the functional group f represents the number 1, the organosilicon compound of formula (II) according to the invention contains a structural grouping —[NR$_7$—(A')]-.

If the functional group h represents the number 1, the organosilicon compound of formula (II) according to the invention contains a structural group —[NR$_8$—(A''')]-.

In this context, R$_7$ and R$_8$ represent, independently of one another, a hydrogen atom, a C$_1$-C$_6$ alkyl group, a hydroxy C$_1$-C$_6$ alkyl group, a C$_2$-C$_6$ alkenyl group, an amino C$_1$-C$_6$ alkyl group or a group of formula (III):

(III).

Most preferably, the functional groups R7 and R8 represent, independently of one another, a hydrogen atom, a methyl group, a 2-hydroxyethyl group, a 2-alkenyl group, a 2-aminoethyl group or a grouping of formula (III).

If the functional group f represents the number 1 and the functional group h represents the number 0, the organosilicon compound according to the invention contains the grouping [NR$_7$—(A')], but not the grouping —[NR$_8$—(A''')]. If the functional group R7 represents a grouping of formula (III), the pretreatment agent (a) contains an organosilicon compound with 3 reactive silane groups.

In another preferred embodiment, an agent according to the invention is characterized in that it contains at least one first organosilicon compound (a1) of formula (II),

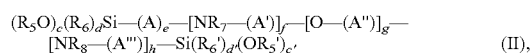

(II), where e and f both represent the number 1, g and h both represent the number 0, A and A' represent, independently of one another, a linear, divalent C$_1$-C$_6$ alkylene group and R7 represents a hydrogen atom, a methyl group, a 2-hydroxyethyl group, a 2-alkenyl group, a 2-aminoethyl group or a grouping of formula (III).

In another preferred embodiment, an agent according to the invention is characterized in that it contains at least one first organosilicon compound (a1) of formula (II), where e and f both represent the number 1, g and h both represent the number 0, A and A' represent, independently of one another, a methylene group (—CH$_2$—), an ethylene group (—CH$_2$—CH$_2$—) or a propylene group (—CH$_2$—CH$_2$—CH$_2$—), and R7 represents a hydrogen atom, a methyl group, a 2-hydroxyethyl group, a 2-alkenyl group, a 2-aminoethyl group or a grouping of formula (III).

To achieve the object according to the invention, suitable organosilicon compounds of formula (II) are:

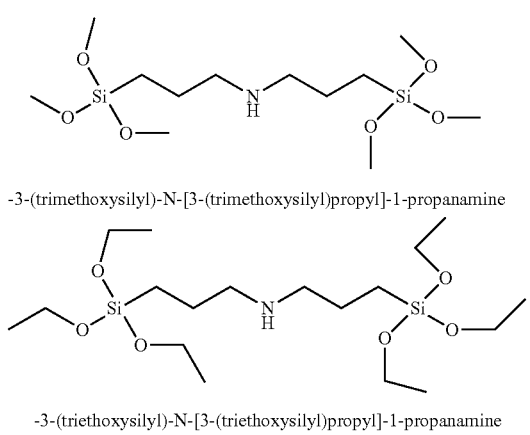

-3-(trimethoxysilyl)-N-[3-(trimethoxysilyl)propyl]-1-propanamine

-3-(triethoxysilyl)-N-[3-(triethoxysilyl)propyl]-1-propanamine

-continued

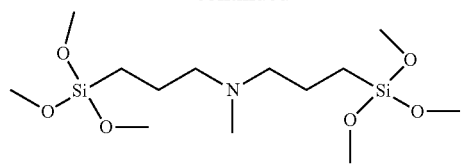

-N-methyl-3-(trimethoxysilyl)-N-[3-(trimethoxysilyl)propyl]-1-propanamine

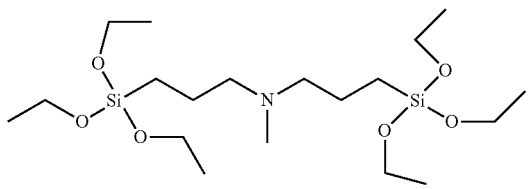

-N-methyl-3-(triethoxysilyl)-N-[3-(triethoxysilyl)propyl]-1-propanamine

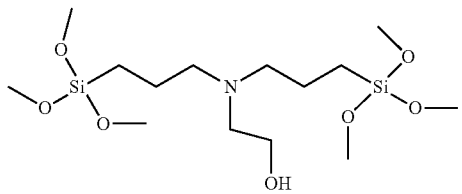

-2-[bis[3-(trimethoxysilyl)propyl]amino]ethanol

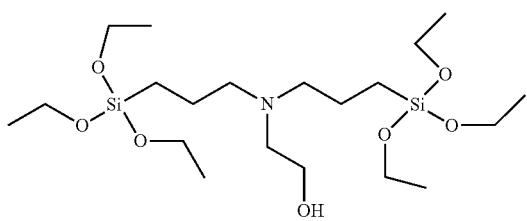

-2-[bis[3-(triethoxysilyl)propyl]amino]ethanol

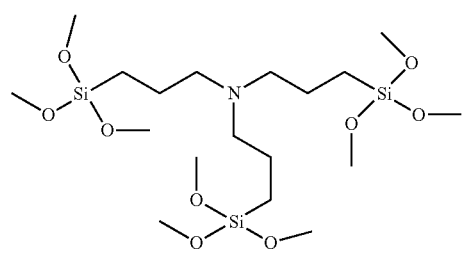

-3-(trimethoxysilyl)-N,N-bis[3-(trimethoxysilyl)propyl]-1-propanamine

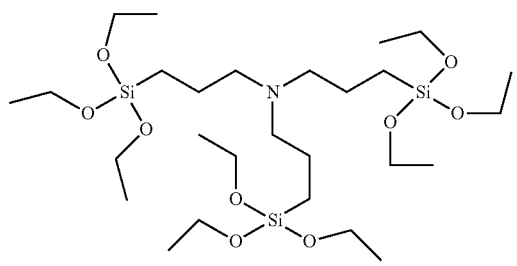

-3-(triethoxysilyl)-N,N-bis[3-(triethoxysilyl)propyl]-1-propanamine

-continued

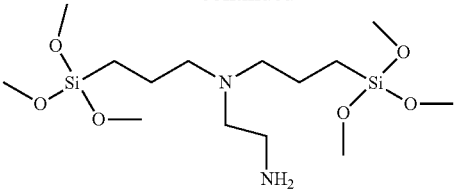

-N1,N1-bis[3-(trimethoxysilyl)propyl]-1,2-ethanediamine

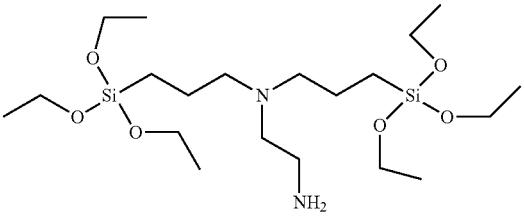

-N1,N1-bis[3-(triethoxysilyl)propyl]-1,2-ethanediamine

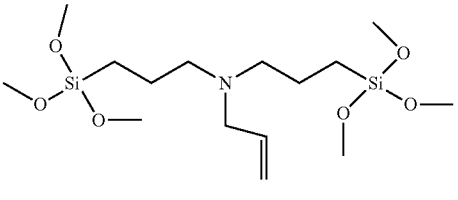

-N,N-bis[3-(trimethoxysilyl)propyl]-2-propen-1-amine

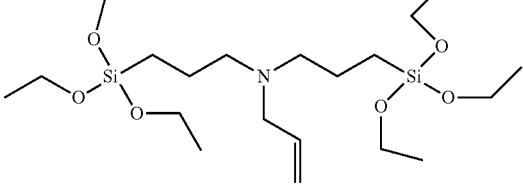

-N,N-bis[3-(triethoxysilyl)propyl]-2-propen-1-amine

The aforementioned organosilicon compounds of formula (II) are commercially available.

Bis(trimethoxysilylpropyl)amine with the CAS number 82985-35-1 can, for example, be purchased from Sigma-Aldrich.

Bis[3-(triethoxysilyl)propyl]amines with the CAS number 13497-18-2 can be purchased from Sigma-Aldrich, for example.

N-methyl-3-(trimethoxysilyl)-N-[3-(trimethoxysilyl)propyl]-1-propanamine is alternatively also referred to as bis (3-trimethoxysilylpropyl)-N-methylamine and can be purchased commercially from Sigma-Aldrich or Fluorochem.

3-(triethoxysilyl)-N,N-bis[3-(triethoxysilyl)propyl]-1-propanamine with the CAS number 18784-74-2 can be purchased, for example, from Fluorochem or Sigma-Aldrich.

In another preferred embodiment, an agent according to the invention is characterized in that it contains at least one first organosilicon compound (a1) of formula (II) selected from the group consisting of:
3-(trimethoxysilyl)-N[3-(trimethoxysilyl)propyl]-1-propanamine
3-(triethoxysilyl)-N-[3-(triethoxysilyl)propyl]-1-propanamine
N-methyl-3-(trimethoxysilyl)-N-[3-(trimethoxysilyl)propyl]-1-propanamine
N-methyl-3-(triethoxysilyl)-N-[3-(triethoxysilyl)propyl]-1-propanamine 2-[bis[3-(trimethoxysilyl)propyl]amino]ethanol
2-[bis[3-(triethoxysilyl)propyl]amino]ethanol
3-(trimethoxysilyl)-N,N-bis[3-(trimethoxysilyl)propyl]-1-propanamine
3-(triethoxysilyl)-N,N-bis[3-(triethoxysilyl)propyl]-1-propanamine
N1,N1-bis[3-(trimethoxysilyl)propyl]-1,2-ethanediamine
N1,N1-bis[3-(triethoxysilyl)propyl]-1,2-ethanediamine
N,N-bis[3-(trimethoxysilyl)propyl]-2-propen-1-amine, and/or
N,N-bis[3-(triethoxysilyl)propyl]-2-propen-1-amine.

In order to achieve colorings having particularly good color fastness and particularly high wash fastness, it has been found to be very advantageous if the agent according to the invention contains, as a second organosilicon compound (a2), at least one organosilicon compound of formula (IV):

$$R_9Si(OR_{10})_k(R_{11})_m \quad (IV).$$

The compounds of formula (IV) are organosilicon compounds selected from silanes with one, two or three silicon atoms, wherein the organosilicon compound comprises one or more hydroxyl groups and/or hydrolyzable groups per molecule.

The organosilicon compound(s) of formula (IV) can also be referred to as silanes of the alkyl alkoxysilanes type or alkyl hydroxysilanes type, $$R_9Si(OR_{10})_k(R_{11})_m \quad (IV),$$

where
$R_9$ represents a $C_1$-$C_{12}$ alkyl group,
$R_{10}$ represents a hydrogen atom or a $C_1$-$C_6$ alkyl group,
$R_{11}$ represents a $C_1$-$C_6$ alkyl group,
k represents an integer from 1 to 3, and
m represents the integer 3-k.

In another preferred embodiment, an agent according to the invention is characterized in that it contains at least one second organosilicon compound (a2) of formula (IV):

$$R_9Si(OR_{10})_k(R_{11})_m \quad (IV),$$

where
$R_9$ represents a $C_1$-$C_{12}$ alkyl group,
$R_{10}$ represents a hydrogen atom or a $C_1$-$C_6$ alkyl group,
$R_{11}$ represents a $C_1$-$C_6$ alkyl group,
k represents an integer from 1 to 3, and
m represents the integer 3-k.

In another preferred embodiment, an agent according to the invention is characterized in that, in addition to the organosilicon compound(s) of formula (I), it contains at least one further organosilicon compound of formula (IV):

$$R_9Si(OR_{10})_k(R_{11})_m \quad (IV),$$

where
$R_9$ represents a $C_1$-$C_{12}$ alkyl group,
$R_{10}$ represents a hydrogen atom or a $C_1$-$C_6$ alkyl group,
$R_{11}$ represents a $C_1$-$C_6$ alkyl group,
k represents an integer from 1 to 3, and
m represents the integer 3-k.

In another preferred embodiment, an agent according to the invention is characterized in that, in addition to the organosilicon compound(s) of formula (II), it contains at least one further organosilicon compound of formula (IV):

$$R_9Si(OR_{10})_k(R_{11})_m \quad (IV),$$

where
$R_9$ represents a $C_1$-$C_{12}$ alkyl group,
$R_{10}$ represents a hydrogen atom or a $C_1$-$C_6$ alkyl group,
$R_{11}$ represents a $C_1$-$C_6$ alkyl group,
k represents an integer from 1 to 3, and
m represents the integer 3-k.

In the organosilicon compounds of formula (IV), the $R_9$ functional group represents a $C_1$-$C_{12}$ alkyl group. This $C_1$-$C_{12}$ alkyl group is saturated and can be linear or branched. $R_9$ preferably represents a linear $C_1$-$C_8$ alkyl group.

Preferably, $R_9$ represents a methyl group, an ethyl group, an n-propyl group, an n-butyl group, an n-pentyl group, an n-hexyl group, an n-octyl group or an n-dodecyl group. Particularly preferably, $R_9$ represents a methyl group, an ethyl group or an n-octyl group.

In the organosilicon compounds of formula (IV), the functional group $R_{10}$ represents a hydrogen atom or a $C_1$-$C_6$ alkyl group. Particularly preferably, $R_{10}$ represents a methyl group or an ethyl group.

In the organosilicon compounds of formula (IV), the Ru functional group represents a $C_1$-$C_6$ alkyl group. Particularly preferably, Ru represents a methyl group or an ethyl group.

Furthermore, k represents an integer from 1 to 3, and m represents the integer 3-k. If k represents the number 3, then m is equal to 0. If k represents the number 2, then m is equal to 1. If k represents the number 1, then m is equal to 2.

Colorings with the best wash fastness were obtained when an agent (a) containing at least one organosilicon compound of formula (IV) where the functional group k represents the number 3 was used in the method. In this case, the functional group m represents the number 0.

To achieve the object according to the invention, particularly well-suited organosilicon compounds of formula (IV) are:

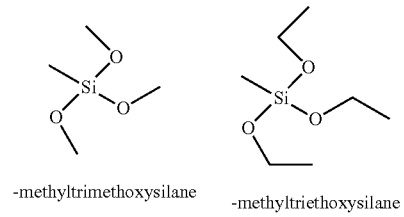
-methyltrimethoxysilane

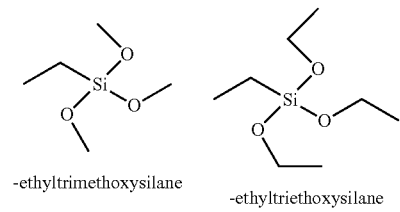
-methyltriethoxysilane

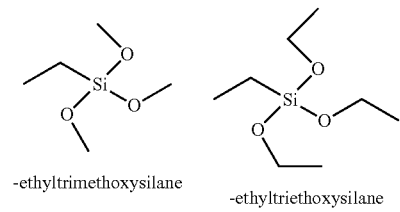
-ethyltrimethoxysilane

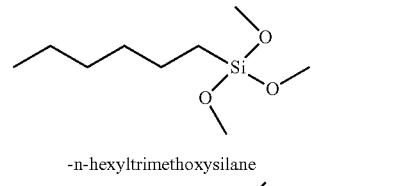
-ethyltriethoxysilane

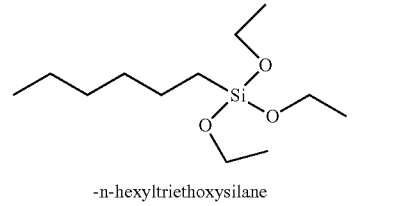
-n-hexyltrimethoxysilane

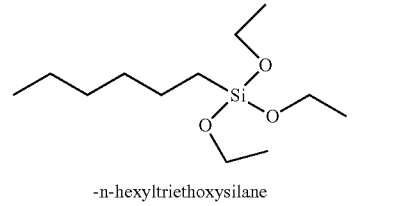
-n-hexyltriethoxysilane

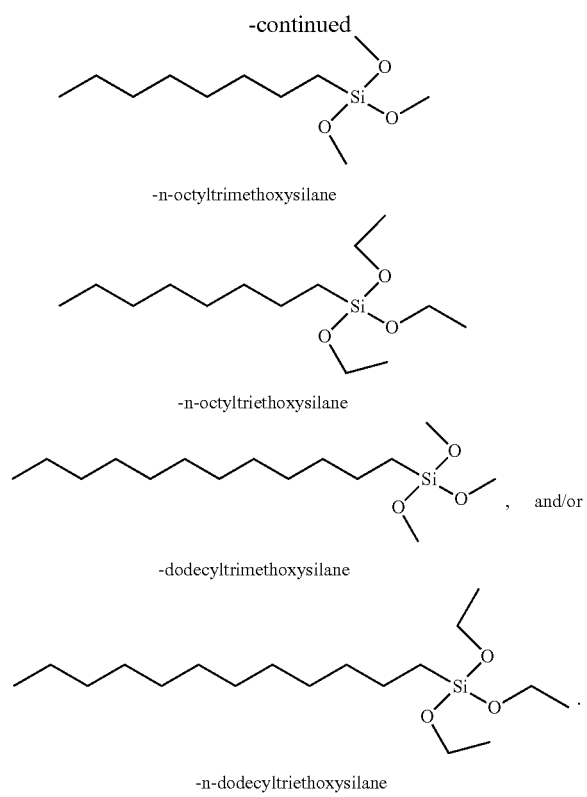

-n-octyltrimethoxysilane

-n-octyltriethoxysilane

-dodecyltrimethoxysilane , and/or

-n-dodecyltriethoxysilane

In another preferred embodiment, an agent according to the invention is characterized in that it contains at least one second organosilicon compound (a2) of formula (IV) selected from the group consisting of:
methyltrimethoxysilane
methyltriethoxysilane
ethyltrimethoxysilane
ethyltriethoxysilane
hexyltrimethoxysilane
hexyltriethoxysilane
octyltrimethoxysilane
octyltriethoxysilane
dodecyltrimethoxysilane, and/or
dodecyltriethoxysilane.

To achieve the object according to the invention, additional particularly well-suited organosilicon compounds are also:
vinyltrimethoxysilane and
vinyltriethoxysi lane.

In an explicitly very particularly preferred embodiment, an agent according to the invention is characterized in that it contains at least one first organosilicon compound (a1) of formula (I) selected from the group consisting of (3-aminopropyl)triethoxysilane and (3-aminopropyl)trimethoxysilane, and additionally contains at least one second organosilicon compound (a2) of formula (IV) selected from the group of methyltrimethoxysilane, methyltriethoxysilane, ethyltrimethoxysilane, ethyltriethoxysilane, hexyltrimethoxysilane and hexyltriethoxysilane.

The organosilicon compounds described above are reactive compounds. In order to achieve particularly good dyeing results, it is particularly advantageous to use the organosilicon compounds of formula (I) and/or (II) in certain ranges of amounts in the agent (a).

In this context, it has been found to be preferable if the agent according to the invention contains, based on the total weight of the agent, one or more organosilicon compounds (a1) from the group of compounds of formulas (I) and (II) in a total amount from 0.1 to 99.0 wt. %, preferably from 0.3 to 33 wt. %, and particularly preferably from 1.5 to 11.0 wt. %.

Within the context of another very particularly preferred embodiment, an agent according to the present invention is characterized in that it contains, based on the total weight of the agent, one or more organosilicon compounds (a1) from the group of compounds of formulas (I) and (II) in a total amount from 0.1 to 99.0 wt. %, preferably from 0.3 to 33 wt. %, and particularly preferably from 1.5 to 11.0 wt. %.

To achieve particularly good dyeing results, it is furthermore of particular advantage to use the organosilicon compounds of formula (IV) in certain ranges of amounts in the agent (a).

Furthermore, a very particularly preferred agent is therefore characterized in that it contains, based on the total weight of the agent, one or more organosilicon compounds (a2) from the group of compounds of formula (IV) in a total amount from 0.1 to 99.0 wt. %, preferably from 0.6 to 66.0 wt. %, and particularly preferably from 3.0 to 22.0 wt. %.

Within the context of another very particularly preferred embodiment, an agent according to the present invention is characterized in that it contains, based on the total weight of the agent, one or more organosilicon compounds (a2) from the group of compounds of formula (IV) in a total amount from 0.1 to 99.0 wt. %, preferably from 0.6 to 66.0 wt. %, and particularly preferably from 3.0 to 22.0 wt. %.

The amounts used of the silanes from groups (a1) and (a2) add up to a maximum of 100 wt. % in the context of this embodiment.

Oligomers or Condensates of Organosilicon Compounds

The organosilicon compounds (a1) according to the invention, in particular those of formula (I) and/or (II) and/or (IV), are reactive compounds which can undergo a hydrolysis and condensation reaction with water.

The reaction of the organic $C_1$-$C_6$ alkoxysilanes with water can take place in various ways. The reaction starts as soon as the $C_1$-$C_6$ alkoxysilanes come into contact with water by mixing. Once $C_1$-$C_6$ alkoxysilanes and water are in contact, an exothermic hydrolysis reaction takes place according to the following scheme (reaction scheme using the example of 3-aminopropyltriethoxy silane):

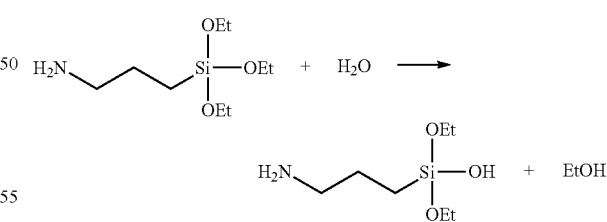

Depending on the number of hydrolyzable $C_1$-$C_6$ alkoxy groups per silane molecule, the hydrolysis reaction can also occur several times per $C_1$-$C_6$ alkoxysilane used:

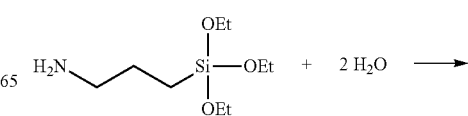

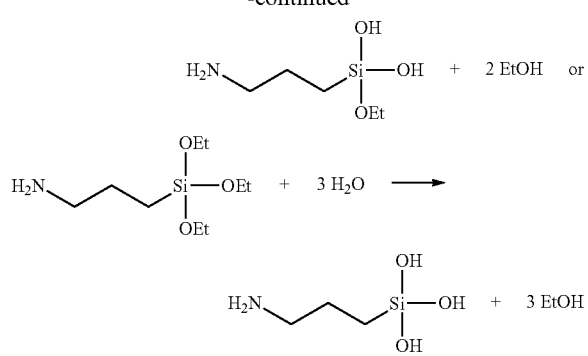

Hydrolysis using the example of methyltrimethoxysilane:

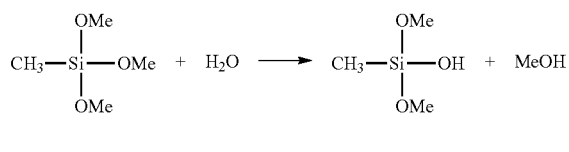

Depending on the amount of water used, the hydrolysis reaction can also be repeated several times per $C_1$-$C_6$ alkoxysilane used:

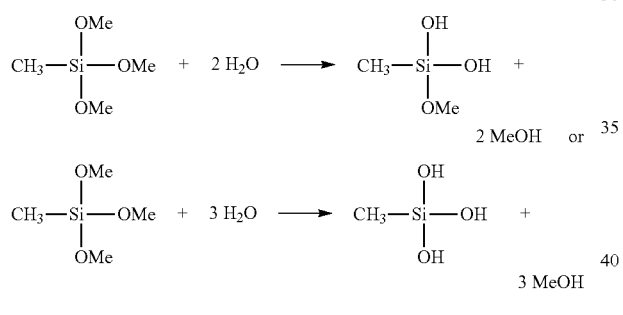

Condensation of the partially (or in parts completely) hydrolyzed $C_1$-$C_6$ alkoxy silanes takes place after hydrolysis, or almost simultaneously with hydrolysis. Precondensation can proceed, for example, according to the following scheme:

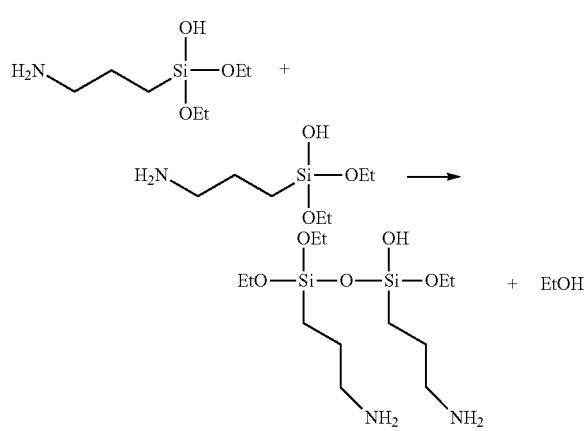

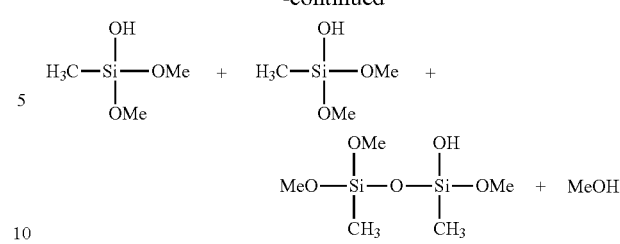

Both partially hydrolyzed and fully hydrolyzed $C_1$-$C_6$ alkoxysilanes can participate in the condensation reaction, undergoing condensation with not yet reacted, partially hydrolyzed or also fully hydrolyzed $C_1$-$C_6$ alkoxysilanes.

Possible condensation reactions are, for example (shown using the mixture (3-aminopropyl)triethoxysilane and methyltrimethoxysilane):

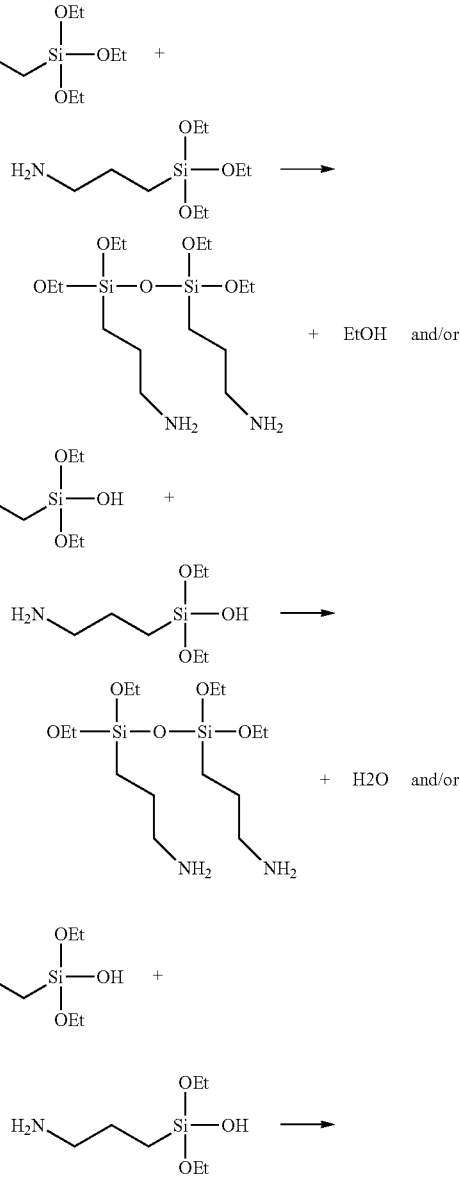

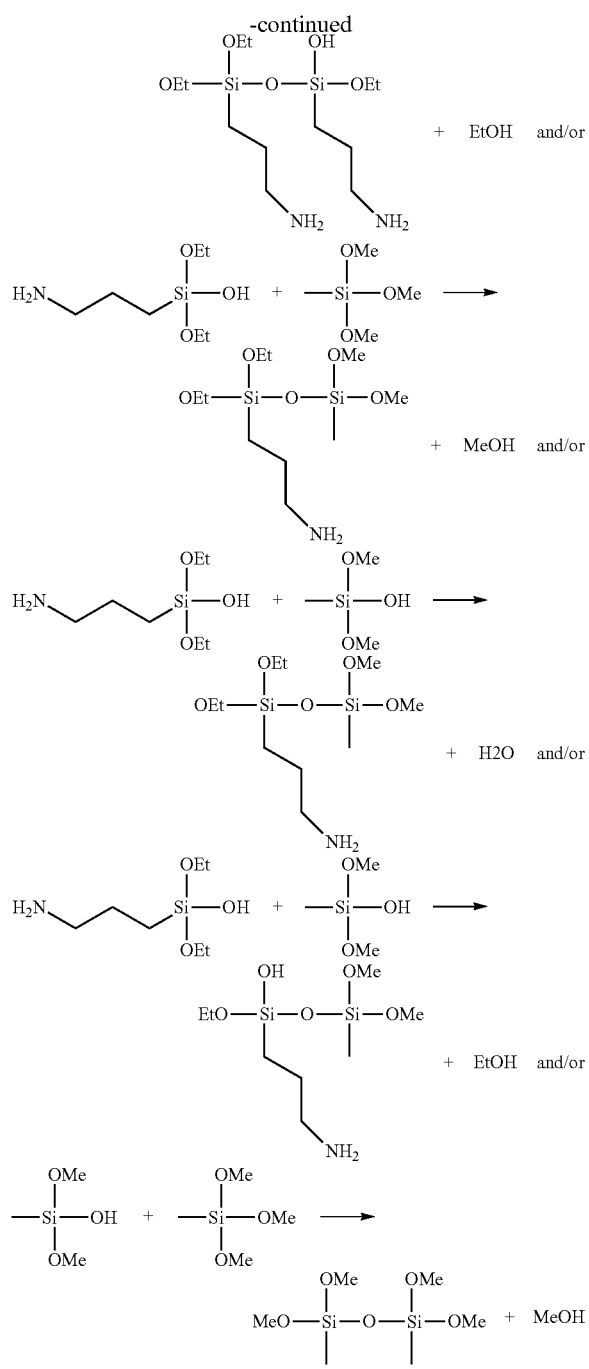

In the above exemplary reaction schemes, the condensation to form a dimer is shown, but further condensations to oligomers with a plurality of silane atoms are also possible and preferred.

This hydrolysis or condensation reaction already starts in the presence of very low amounts of water, and therefore the oligomers and/or condensation products of the aforementioned organosilicon compounds are also encompassed by this invention.

In the context of a further embodiment, an agent for coloring keratin material, in particular human hair, is therefore preferred, containing:
(a) at least two different organosilicon compounds, the oligomers and/or the condensation products thereof, wherein each organosilicon compound is selected independently of the other from silanes with one, two or three silicon atoms, and the organosilicon compound comprises one or more hydroxyl groups and/or hydrolyzable groups per molecule,
(b) at least one pigment, and
(c) at least one fatty component that is liquid at 20° C. and/or an organic solvent.

Pigments (b)

As the second essential component, the agent according to the invention contains at least one pigment (b).

Pigments within the meaning of the present invention are understood to mean dyeing compounds which have a solubility of less than 0.5 g/L, preferably of less than 0.1 g/L, even more preferably of less than 0.05 g/L, at 25° C. in water. The method described below, for example, can be used to determine water solubility: 0.5 g of the pigment is weighed out in a beaker. A stir bar is added. Then one liter of distilled water is added. This mixture is heated to 25° C. while stirring with a magnetic stirrer for one hour. If still undissolved components of the pigment are visible in the mixture after this period, the solubility of the pigment is below 0.5 g/L. If the pigment-water mixture cannot be visually assessed due to the high intensity of the pigment that may be finely dispersed, the mixture is filtered. If a portion of undissolved pigments remains on the filter paper, the solubility of the pigment is below 0.5 g/L.

Suitable pigments or color pigments may be of inorganic and/or organic origin.

In a preferred embodiment, an agent (b) according to the invention is characterized in that it contains at least one dyeing compound from the group of inorganic and/or organic pigments.

Preferred color pigments are selected from synthetic or natural inorganic pigments. Inorganic color pigments of natural origin can be produced, for example, from chalk, ocher, umbra, green soil, burnt Sienna or graphite. Furthermore, black pigments such as, for example, iron oxide black, chromatic pigments such as, for example, ultramarine or iron oxide red, and also fluorescent or phosphorescent pigments, can be used as inorganic color pigments.

Colored metal oxides, hydroxides and oxide hydrates, mixed phase pigments, sulfur-containing silicates, silicates, metal sulfides, complex metal cyanides, metal sulfates, chromates and/or molybdates are particularly suitable. Particularly preferred color pigments are black iron oxide (CI 77499), yellow iron oxide (CI 77492), red and brown iron oxide (CI 77491), manganese violet (CI 77742), ultramarine (sodium aluminum sulphosilicates, CI 77007, Pigment Blue 29), chromium oxide hydrate (CI 77289), Iron Blue ferric ferrocyanide, CI 77510) and/or carmine (cochineal).

Color pigments which are likewise particularly preferred according to the invention are colored pearlescent pigments. These are usually based on mica and may be coated with one or more metal oxides. Mica is a phyllosilicate. The most important representatives of these silicates are muscovite, phlogopite, paragonite, biotite, lepidolite, and margarite. In order to produce the pearlescing pigments in conjunction with metal oxides, mica, primarily muscovite or phlogopite, is coated with a metal oxide.

As an alternative to natural mica, synthetic mica coated with one or more metal oxides(s) can also be used as a pearlescent pigment. Particularly preferred pearlescent pigments are based on natural or synthetic mica and are coated with one or more of the aforementioned metal oxides. The color of the respective pigments can be varied by varying the layer thickness of the metal oxide(s).

In another preferred embodiment, an agent according to the invention is characterized in that it contains at least one pigment selected from the group of colored metal oxides, metal hydroxides, metal oxide hydrates, silicates, metal sulfides, complex metal cyanides, metal sulphates, bronze pigments and/or from mica-based colored pigments which are coated with at least one metal oxide and/or a metal oxychloride.

In another preferred embodiment, an agent according to the invention is characterized in that it contains (b) a pigment selected from mica-based colored pigments which are coated with one or more metal oxides from the group of titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, pigment blue 29), chromium oxide hydrate (CI 77289), chromium oxide (CI 77288) and/or iron blue (ferric ferrocyanide, CI 77510).

Examples of particularly suitable color pigments are commercially available, for example, under the trade names Rona®, Colorona®, Xirona®, Dichrona® and Timiron® from the company Merck, Ariabel@ and Unipure® from the company Sensient, Prestige® from the company Eckart Cosmetic Colors, and Sunshine® from the company Sunstar.

Very particularly preferred color pigments with the trade name Colorona® are, for example:
- Colorona Copper, Merck, MICA, CI 77491 (IRON OXIDES)
- Colorona Passion Orange, Merck, Mica, CI 77491 (Iron Oxides), Alumina
- Colorona Patina Silver, Merck, MICA, CI 77499 (IRON OXIDES), CI 77891 (TITANIUM DIOXIDE)
- Colorona RY, Merck, CI 77891 (TITANIUM DIOXIDE), MICA, CI 75470 (CARMINE)
- Colorona Oriental Beige, Merck, MICA, CI 77891 (TITANIUM DIOXIDE), CI 77491 (IRON OXIDES)
- Colorona Dark Blue, Merck, MICA, TITANIUM DIOXIDE, FERRIC FERROCYANIDE
- Colorona Chameleon, Merck, CI 77491 (IRON OXIDES), MICA
- Colorona Aborigine Amber, Merck, MICA, CI 77499 (IRON OXIDES), CI 77891 (TITANIUM DIOXIDE)
- Colorona Blackstar Blue, Merck, CI 77499 (IRON OXIDES), MICA
- Colorona Patagonian Purple, Merck, MICA, CI 77491 (IRON OXIDES), CI 77891 (TITANIUM DIOXIDE), CI 77510 (FERRIC FERROCYANIDE)
- Colorona Red Brown, Merck, MICA, CI 77491 (IRON OXIDES), CI 77891 (TITANIUM DIOXIDE)
- Colorona Russet, Merck, CI 77491 (TITANIUM DIOXIDE), MICA, CI 77891 (IRON OXIDES)
- Colorona Imperial Red, Merck, MICA, TITANIUM DIOXIDE (CI 77891), D&C RED NO. 30 (CI 73360)
- Colorona Majestic Green, Merck, CI 77891 (TITANIUM DIOXIDE), MICA, CI 77288 (CHROMIUM OXIDE GREENS)
- Colorona Light Blue, Merck, MICA, TITANIUM DIOXIDE (CI 77891), FERRIC FERROCYANIDE (CI 77510)
- Colorona Red Gold, Merck, MICA, CI 77891 (TITANIUM DIOXIDE), CI 77491 (IRON OXIDES)
- Colorona Gold Plus MP 25, Merck, MICA, TITANIUM DIOXIDE (CI 77891), IRON OXIDES (CI 77491)
- Colorona Carmine Red, Merck, MICA, TITANIUM DIOXIDE, CARMINE
- Colorona Blackstar Green, Merck, MICA, CI 77499 (IRON OXIDES)
- Colorona Bordeaux, Merck, MICA, CI 77491 (IRON OXIDES)
- Colorona Bronze, Merck, MICA, CI 77491 (IRON OXIDES)
- Colorona Bronze Fine, Merck, MICA, CI 77491 (IRON OXIDES)
- Colorona Fine Gold MP 20, Merck, MICA, CI 77891 (TITANIUM DIOXIDE), CI 77491 (IRON OXIDES)
- Colorona Sienna Fine, Merck, CI 77491 (IRON OXIDES), MICA
- Colorona Sienna, Merck, MICA, CI 77491 (IRON OXIDES)
- Colorona Precious Gold, Merck, Mica, CI 77891 (Titanium dioxide), Silica, CI 77491 (Iron Oxides), Tin oxide
- Colorona Sun Gold Sparkle MP 29, Merck, MICA, TITANIUM DIOXIDE, IRON OXIDES, MICA, CI 77891, CI 77491 (EU)
- Colorona Mica Black, Merck, CI 77499 (Iron oxides), Mica, CI 77891 (Titanium dioxide)
- Colorona Bright Gold, Merck, Mica, CI 77891 (Titanium dioxide), CI 77491 (Iron oxides)
- Colorona Blackstar Gold, Merck, MICA, CI 77499 (IRON OXIDES)

Additional particularly preferred color pigments with the trade name Xirona® are, for example:
- Xirona Golden Sky, Merck, Silica, CI 77891 (Titanium Dioxide), Tin Oxide
- Xirona Caribbean Blue, Merck, Mica, CI 77891 (Titanium Dioxide), Silica, Tin Oxide
- Xirona Kiwi Rose, Merck, Silica, CI 77891 (Titanium Dioxide), Tin Oxide
- Xirona Magic Mauve, Merck, Silica, CI 77891 (Titanium Dioxide), Tin Oxide.

In addition, particularly preferred color pigments with the trade name Unipure® are, for example:
- Unipure Red LC 381 EM, Sensient CI 77491 (Iron Oxides), Silica
- Unipure Black LC 989 EM, Sensient, CI 77499 (Iron Oxides), Silica
- Unipure Yellow LC 182 EM, Sensient, CI 77492 (Iron Oxides), Silica In another embodiment, the agent according to the invention can also contain (b) one or more dyeing compounds from the group of organic pigments.

The organic pigments according to the invention are correspondingly insoluble organic dyes or color lakes which may be selected, for example, from the group of nitroso, nitro, azo, xanthene, anthraquinone, isoindolinone, isoindoline, quinacridone, perinone, perylene, diketopyrrolopyorrole, indigo, thioindido, dioxazine, and/or triarylmethane compounds.

Particularly well suited organic pigments can for example include carmine, quinacridone, phthalocyanine, sorghum, blue pigments with the Color Index numbers CI 42090, CI 69800, CI 69825, CI 73000, CI 74100 or CI 74160, yellow pigments with the Color Index numbers CI 11680, CI 11710, CI 15985, CI 19140, CI 20040, CI 21100, CI 21108, CI 47000 or CI 47005, green pigments with the Color Index numbers CI 61565, CI 61570 or CI 74260, orange pigments with the Color Index numbers CI 11725, CI 15510, CI 45370 or CI 71105, and red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In another particularly preferred embodiment, an agent according to the invention is characterized in that it contains at least one organic pigment selected from the group of carmine, quinacridone, phthalocyanine, sorghum, blue pigments with the Color Index numbers CI 42090, CI 69800, CI 69825, CI 73000, CI 74100 or CI 74160, yellow pigments with the Color Index numbers CI 11680, CI 11710, CI 15985, CI 19140, CI 20040, CI 21100, CI 21108, CI 47000 or CI 47005, green pigments with the Color Index numbers CI 61565, CI 61570 or CI 74260, orange pigments with the Color Index numbers CI 11725, CI 15510, CI 45370 or CI 71105, and red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

The organic pigment can also be a color lake. The term color lake within the meaning of the invention is understood to mean particles which comprise a layer of absorbed dyes, with the unit consisting of particles and dye being insoluble under the above-mentioned conditions. The particles may be, for example, inorganic substrates which may be aluminum, silica, calcium borosilicate, calcium aluminum borosilicate or aluminum.

For example, the alizarin color lake can be used as the color lake.

Pigments with a specific shaping can also have been used to color the keratin material. For example, a pigment based on a lamellar and/or lenticular substrate plate can be used. Furthermore, dyeing is also possible based on a substrate plate which comprises a vacuum-metalized pigment.

In the context of another embodiment, a method according to the invention can be characterized in that the corresponding agent also comprises one or more dyeing compounds from the group of pigments based on a lamellar substrate plate, pigments based on a lenticular substrate plate, and vacuum-metalized pigments.

The substrate plates of this type have an average thickness of at most 50 nm, preferably less than 30 nm, particularly preferably at most 25 nm, for example at most 20 nm. The average thickness of the substrate plates is at least 1 nm, preferably at least 2.5 nm, particularly preferably at least 5 nm, for example at least 10 nm. Preferred ranges for the thickness of the substrate plates are 2.5 to 50 nm, 5 to 50 nm, 10 to 50 nm; 2.5 to 30 nm, 5 to 30 nm, 10 to 30 nm; 2.5 to 25 nm, 5 to 25 nm, 10 to 25 nm, 2.5 to 20 nm, 5 to 20 nm and 10 to 20 nm. Preferably, each substrate plate has as uniform a thickness as possible.

Due to the small thickness of the substrate plates, the pigment has a particularly high covering power.

The substrate plates have a monolithic structure. Monolithic in this context means consisting of a single self-contained unit without fractures, stratifications or inclusions, although structural changes may, however, occur within the substrate plates. The substrate plates are preferably composed homogeneously, i.e. there is no concentration gradient within the plates. In particular, the substrate plates are not composed in layers and do not have any particles distributed therein.

The size of the substrate plate can be matched to the respective application, in particular to the desired effect on the keratin material. As a rule, the substrate plates have a mean maximum diameter of approximately 2 to 200 μm, in particular approximately 5 to 100 μm.

In a preferred embodiment, the form factor (aspect ratio), expressed by the ratio of the average size to the average thickness, is at least 80, preferably at least 200, more preferably at least 500, particularly preferably more than 750. The average size of the uncoated substrate plates is understood to mean the d50 value of the uncoated substrate plates. Unless stated otherwise, the d50 value was determined with a Sympatec Helos-type device with Quixel wet dispersion. To prepare the sample, the sample to be investigated was pre-dispersed in isopropanol for a period of 3 minutes.

The substrate plates may be composed of any material that can be converted into the form of a plate.

They can be of natural origin, but can also be produced synthetically. Materials from which the substrate plates can be composed are, for example, metals and metal alloys, metal oxides, preferably aluminum oxide, inorganic compounds and minerals such as mica and (semi)precious stones, as well as plastics. Preferably, the substrate plates are made of metal (alloys).

Any metal suitable for metallic luster pigments is suitable as the metal. Such metals are, inter alia, iron and steel, and all air-resistant and water-resistant (semi) metals such as, for example, platinum, zinc, chromium, molybdenum and silicon, as well as alloys thereof such as aluminum bronzes and brass. Preferred metals are aluminum, copper, silver and gold. Preferred substrate plates are aluminum plates and brass plates, wherein substrate plates made of aluminum are particularly preferred.

Lamellar substrate plates are characterized by an irregularly structured edge and are also referred to as "cornflakes" due to their appearance.

Due to their irregular structure, pigments based on lamellar substrate plates produce a large amount of scattered light. In addition, pigments based on lamellar substrate plates do not completely cover the existing color of a keratin material, and effects analogous to natural graying can be achieved, for example.

Lenticular (=lens-shaped) substrate plates have a substantially round edge and are also referred to as "silver dollars" due to their appearance. Due to their regular structure, pigments based on lenticular substrate plates have the predominance of reflected light.

Vacuum metalized pigments (VMP) can be obtained, for example, by releasing metals, metal alloys or metal oxides of correspondingly coated films. They are characterized by a particularly small thickness of the substrate plates within a range of 5 to 50 nm and by a particularly smooth surface with increased reflectivity. Substrate plates which comprise a pigment metalized in a vacuum are also referred to as VMP substrate plates in the context of this application. VMP substrate plates of aluminum can be obtained, for example, by releasing aluminum from metalized films.

The substrate plates made of metal or metal alloy can be passivated, for example by anodizing (oxide layer) or chromating.

Uncoated lamellar, lenticular and/or VPM substrate plates, in particular those made of metal or metal alloy, reflect the incident light to a high degree and produce a light-dark flop, but no impression of color.

An impression of color can be produced, for example, from optical interference effects. Such pigments can be based on at least single-coated substrate plates. These manifest interference effects by superimposing differently refracted and reflected light beams.

Accordingly, preferred pigments are pigments based on a coated lamellar substrate plate. The substrate plate preferably has at least one coating B of a highly refractive metal oxide with a coating thickness of at least 50 nm. A coating A is preferably still between the coating B and the surface of the substrate plate. Optionally, another coating C, which is different from the underlying layer B, is on the layer B.

Suitable materials for coatings A, B and C are all substances that can be applied to the substrate plates in a film-like and permanent manner and, in the case of coatings A and B, have the required optical properties. In general, a coating of a part of the surface of the substrate plates is sufficient to obtain a pigment with a glossy effect. Thus, for example, only the upper and/or lower side of the substrate plates can be coated, wherein the side face(s) are omitted. Preferably, the entire surface of the optionally passivated substrate plates, including the side surfaces, is covered by coating B. The substrate plates are therefore completely enveloped by coating B. This improves the optical properties of the pigment and increases the mechanical and chemical resilience the pigments. The above also applies to layer A and preferably also to layer C, if present.

Although a plurality of coatings A, B and/or C can always be present, the coated substrate plates preferably each have only one coating A, B and, if present, C.

The coating B is composed of at least one highly refractive metal oxide. Highly refractive materials have a refractive index of at least 1.9, preferably at least 2.0, and particularly preferably at least 2.4. The coating B preferably comprises at least 95 wt. %, particularly preferably at least 99 wt. %, of highly refractive metal oxide(s).

The coating B has a thickness of at least 50 nm. The thickness of coating B is preferably not more than 400 nm, particularly preferably at most 300 nm.

Highly refractive metal oxides suitable for coating B are preferably selectively light-absorbing (i.e. colored) metal oxides such as iron(III) oxide (α- and γ-Fe2O3, red), cobalt (II) oxide (blue), chromium(III) oxide (green), titanium(III) oxide (blue, usually in a mixture with titanium oxynitrides and titanium nitrides) and vanadium(V) oxide (orange) and mixtures thereof. Also suitable are colorless, highly-refractive oxides such as titanium dioxide and/or zirconium oxide.

Coating B can contain a selectively absorbing dye, preferably 0.001 to 5 wt. %, particularly preferably 0.01 to 1 wt. %, in each case based on the total amount of the coating B. Organic and inorganic dyes which can be stably incorporated into a metal oxide coating are suitable.

The coating A preferably has at least one low-refractive metal oxide and/or metal oxide hydrate. Preferably, coating A comprises at least 95 wt. %, particularly preferably at least 99 wt. %, low-refractive metal oxide (hydrate). Low-refractive materials have a refractive index of at most 1.8, preferably at most 1.6.

The low-refractive metal oxides suitable for coating A include, for example, silicon (di)oxide, silicon oxide hydrate, aluminum oxide, aluminum oxide hydrate, boric oxide, germanium oxide, manganese oxide, magnesium oxide and mixtures thereof, with silicon dioxide being preferred. The coating A preferably has a thickness from 1 to 100 nm, particularly preferably 5 to 50 nm, in particular preferably 5 to 20 nm.

The distance between the surface of the substrate plates and the inner surface of coating B is preferably at most 100 nm, particularly preferably at most 50 nm, in particular preferably at most 20 nm. Because the thickness of coating A and therefore the distance between the surface of the substrate plates and coating B is in the range indicated above, it can be ensured that the pigments have a high covering power.

If the pigment has only one layer A based on a lamellar substrate plate, it is preferred that the pigment has a lamellar substrate plate of aluminum and a layer A of silicon dioxide. If the pigment has a layer A and a layer B based on a lamellar substrate plate, it is preferred that the pigment has a lamellar substrate plate of aluminum, a layer A of silicon dioxide, and a layer B of iron oxide.

According to a preferred embodiment, the pigments have another coating C of a metal oxide (hydrate) different from the underlying coating B. Suitable metal oxides are, for example, silicon (di)oxide, silicon oxide hydrate, aluminum oxide, aluminum oxide hydrate, zinc oxide, tin oxide, titanium dioxide, zirconium oxide, iron(III) oxide and chromium(III) oxide. Silicon dioxide is preferred.

The coating C preferably has a thickness of 10 to 500 nm, particularly preferably 50 to 300 nm. By providing the coating C, for example based on $TiO_2$, better interference can be achieved, while high covering power is maintained.

Layers A and C are in particular for corrosion protection as well as for chemical and physical stabilization. The layers A and C particularly preferably contain silicon dioxide or aluminum oxide which are applied by the sol gel method. This method comprises dispersing the uncoated lamellar substrate plates, or the lamellar substrate plates already coated with layer A and/or layer B, in a solution of a metal alkoxide such as tetraethyl orthosilicate or aluminum triisopropanolate (usually in a solution of organic solvent or a mixture of organic solvent and water with at least 50 wt. % organic solvent such as a C1 to C4 alcohol), and adding a weak base or acid for hydrolyzing the metal alkoxide, thereby forming a film of the metal oxide on the surface of the (coated) substrate plates.

Layer B can be produced, for example, by hydrolytic decomposition of one or more organic metal compounds and/or by precipitation of one or more dissolved metal salts and an optional subsequent post-treatment (for example, transferring formed hydroxide-containing layers into the oxide layers by tempering).

Although each of the coatings A, B and/or C can be composed of a mixture of two or more metal oxide (hydrates), each of the coatings is preferably composed of a metal oxide (hydrate).

The pigments based on coated lamellar or lenticular substrate plates or the pigments based on coated VMP substrate plates preferably have a thickness from 70 to 500 nm, particularly preferably 100 to 400 nm, in particular preferably 150 to 320 nm, for example 180 to 290 nm. Due to the small thickness of the substrate plates, the pigment has a particularly high covering power. The small thickness of the coated substrate plates is achieved in particular because the thickness of the uncoated substrate plates is low, but also because the thicknesses of the coatings A and, if present, C are set to the smallest possible value. The thickness of coating B determines the color impression of the pigment.

The adhesion and abrasion resistance of pigments based on coated substrate plates in the keratin material can be significantly increased by additionally modifying the outermost layer, depending on the structure of layer A, B or C, using organic compounds such as silanes, phosphoric acid esters, titanates, borates or carboxylic acids. The organic compounds are bonded to the surface of the outermost, preferably metal oxide-containing layer A, B or C. The outermost layer refers to the layer spatially furthest removed from the lamellar substrate plate. The organic compounds are preferably functional silane compounds which can bind to the metal oxide-containing layer A, B or C. These may be either monofunctional or bifunctional compounds.

Examples of bifunctional organic compounds include methacryloxypropenyltrimethoxysilane, 3-methacryloxypropyltrimethoxysilane, 3-acryloxypropyltrimethoxysilane, 2-acryloxyethyltrimethoxysilane, 3-methacryloxy-propyltriethoxysilane, 3-acryloxypropyltrimethoxysilane, 2-methacryloxyethyltriethoxysilane, 2-acryloxyethyltriethoxysilane, 3-methacryloxypropyltris(methoxyethoxy)silane, 3-methacryloxypropyltris(butoxyethoxy)silane, 3-methacryloxypropyltris(propoxy)silane, 3-methacryloxypropyltris(butoxy)silane, 3-acryloxy-propyltris(methoxyethoxy)silane, 3-acryloxypropyltris(butoxyethoxy)silane, 3-acryloxypropyltris(butoxy)silane, vinyltrimethoxysilane, vinyltriethoxysilane, vinylethyldichlorosilane, vinylmethyldiacetoxysilane, vinylmethyldichlorosilane, vinylmethyldiethoxysilane, vinyltriacetoxysilane, vinyltrichlorosilane, phenylvinyldiethoxysilane, or phenylallyldichlorosilane. Furthermore, a modification with a monofunctional silane, in particular an alkylsilane or arylsilane, can take place. This has only one functional group which can bind covalently to the surface pigment based on coated lamellar substrate plates (i.e., to the outermost metal oxide-containing layer) or, when the covering is not complete, to the metal surface. The hydrocarbon functional group of the silane faces away from the pigment. Depending on the type and nature of the hydrocarbon functional group of the silane, a different degree of hydrophobicity of the pigment is achieved. Examples of such silanes are hexadecyltrimethoxysilane, propyltrimethoxysilane, etc. Particularly preferably, pigments based on silica-coated aluminum substrate plates are surface-modified with a monofunctional silane. Octyltrimethoxysilane, octyltriethoxysilane, hexadecyltrimethoxysilane and hexadecyltriethoxysilane are particularly preferred. As a result of the altered surface properties/hydrophobization, an improvement in terms of adhesion, abrasion resistance and orientation in the application can be achieved.

Suitable pigments based on a lamellar substrate plate comprise, for example, the pigments of the VISIONAIRE series by Eckart.

Pigments based on a lenticular substrate plate are available, for example, under the name of Alegrace® Gorgeous from the company Schlenk Metallic Pigments GmbH.

Pigments based on a substrate plate, which comprises a vacuum-metalized pigment, are available, for example, under the name of Alegrace® Mavelous or Allegrace® Aurous from the company Schlenk Metallic Pigment GmbH.

Owing to their excellent light and temperature resistance, the use of the aforementioned pigments in the agent (b) of the method according to the invention is very particularly preferred. It is further preferred if the pigments used have a certain particle size. It is therefore advantageous according to the invention if the at least one pigment has an average particle size $D_{50}$ from 1.0 to 50 μm, preferably from 5.0 to 45 μm, preferably from 10 to 40 μm, in particular from 14 to 30 μm. The average particle size $D_{50}$ can be determined, for example, using dynamic light scattering (DLS).

The pigment or pigments can preferably be used in an amount from 1.0 to 20.0 wt. %, preferably from 5.0 to 10.0 wt. %, in each case based on the total weight of the agent.

In another particularly preferred embodiment, an agent according to the invention is characterized in that it contains, based on the total weight of the agent, one or more pigments (b) in a total amount from 1.0 to 20.0 wt. %, preferably from 5.0 to 10.0 wt. %.

Liquid Fats and/or Organic Solvents (c)

As a third component or substance class (c) essential to the invention, the agent according to the invention contains at least one compound from the group of fatty components that are liquid at 20° C. and organic solvents.

The liquid fats and/or the organic solvents (c) ensure fine dispersion of the pigments and provide homogeneous mixing with the silanes (a), in particular with the particularly preferred silanes (a1) and (a2) described above. At the same time, the addition of the fatty components or solvents increases the storage stability of the agent.

"Fatty components," within the context of the invention are understood to be organic compounds with a solubility in water of less than 1 wt. %, and preferably less than 0.1 wt. % at room temperature (22° C.) and atmospheric pressure (760 mmHg). A fatty component liquid at 20° C. has a melting point below 20° C. (measured under atmospheric pressure (760 mmHg)).

The definition of fatty components also explicitly includes only uncharged (i.e. non-ionic) compounds. Fatty components have at least one saturated or unsaturated alkyl group having at least 8 C atoms. The molecular weight of the fatty component is at most 5,000 g/mol, preferably at most 2,500 g/mol, and particularly preferably at most 1,000 g/mol. The fatty components are neither polyoxyalkylated nor polyglycerylated compounds.

Preferred fatty components in this context are the components from the group of $C_{12}$-$C_{30}$ fatty acid triglycerides, $C_{12}$-$C_{30}$ fatty acid diglycerides of $C_{12}$-$C_{30}$ fatty alcohols and/or hydrocarbons, with the proviso that each compound from the above-mentioned substance classes has a melting point below 20° C. Within the meaning of the present invention only non-ionic substances are explicitly considered as fatty components.

Charged compounds, such as fatty acids and salts thereof, are not understood to be fatty components.

Fatty components (c) which are most suitable can be selected from the group of linear or cyclic silicone oils, hydrocarbon oils, liquid fatty acid triglycerides, liquid fatty alcohols, ester oils and mixtures thereof.

In the context of another very particularly preferred embodiment, an agent according to the invention is characterized in that it contains at least one fatty component (c) that is liquid at 20° C. and is selected from the group of linear or cyclic silicone oils, hydrocarbon oils, liquid fatty acid triglycerides, liquid fatty alcohols, ester oils and mixtures thereof.

Silicone oils can also be referred to as oligoalkylsiloxanes and polyalkylsiloxanes which are liquid at 20° C., i.e. the silicone oils have a melting point which is below 20° C. (at atmospheric pressure (760 mmHg)). Preferred linear silicone oils are oligoalkylsiloxanes of general formula (V):

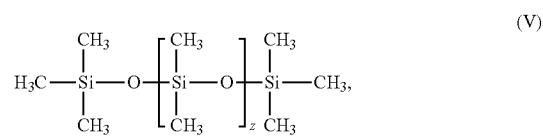

where z denotes an integer from 0 to 10,000, preferably an integer from 0 to 1,000, more preferably an integer from 0 to 100, and very particularly preferably an integer from 0 to 10.

Very particularly preferred linear oligoalkylsiloxanes are, for example:

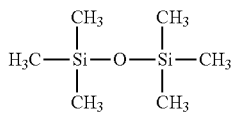
-hexamethyldisiloxane

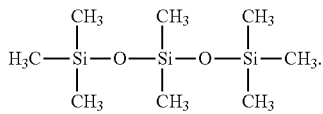
-octamethyltrisiloxane

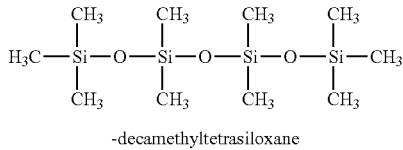
-decamethyltetrasiloxane

Hexamethyldisiloxane has the CAS number 107-46-0 and can be purchased commercially, for example, from Sigma-Aldrich.

Octamethyltrisiloxane has the CAS number 107-51-7 and is also commercially available from Sigma-Aldrich.

Decamethyltetrasiloxane has the CAS number 141-62-8 and is also commercially available from Sigma-Aldrich.

Another particularly well-suited silicone oil can be purchased commercially, for example, under the trade name of Dimethicone Fluid 5 cSt from the company Clearco. This silicone oil has the generic name of polydimethylsiloxane and has the CAS number 63148-62-9. The substance is a clear, colorless and odorless liquid, low-viscosity oil.

Another silicone oil that is particularly well suitable is commercially available under the trade name of Xiameter PMX 200 (1.5 cSt) from Dow Corning. This oil is also a dimethicone or polydimethylsiloxane which has the CAS number 63148-62-9.

Preferred cyclic oligoalkylsiloxanes are compounds of the general formula (VI)

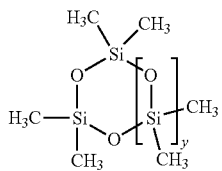

where y represents an integer from 1 to 5. Z preferably represents the numbers 1, 2 or 3.

Very particularly preferred cyclic oligoalkylsiloxanes are, for example:

hexamethylcyclotrisiloxane octamethylcyclotetrasiloxane decamethylcyclopentasiloxane In another preferred embodiment, an agent according to the invention is characterized in that it contains, as the fatty component (c), at least one silicone oil of formula (V) and/or (VI),

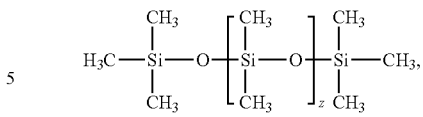

where z denotes an integer from 0 to 10,000, preferably an integer from 0 to 1,000, more preferably an integer from 0 to 100, and very particularly preferably an integer from 0 to 10,

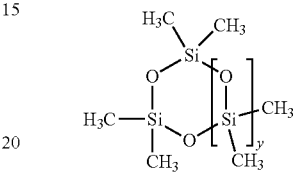

where y represents an integer from 1 to 5, preferably an integer from 1 to 3.

In another preferred embodiment, an agent according to the invention is characterized in that it contains at least one oligoalkylsiloxane (c) which is selected from the group of hexamethyldisiloxane, octamethyltrisiloxane, decamethyltetrasiloxane, hexamethylcyclotrisiloxane, octamethylcyclotetrasiloxane and/or decamethylcyclopentasiloxane.

In contrast to the reactive organosilicon compounds, i.e. the silanes of formulas (I), (II) and (IV), the oligoalkylsiloxanes are composed exclusively of dialkylsilyl groups (in particular dimethylsilyl groups) and trialkylsilyl groups (in particular trimethylsilyl groups) which are linked to one another via oxygen atoms. Thus, the oligoalkylsiloxanes within the meaning of this invention are themselves not reactive compounds and also have no hydrolyzable groups.

Hydrocarbon oils are also particularly suitable fatty components that are liquid at 20° C.

Hydrocarbons are compounds have eight to 80 C atoms composed exclusively of carbon and hydrogen atoms. In this context, aliphatic hydrocarbons such as mineral oils, liquid paraffin oils (e.g., paraffinum liquidum or paraffinum perliquidum), isoparaffin oils and polydecenes are in particular preferred. The hydrocarbons according to the invention are also characterized in that they have a melting point which is below 20° C. under atmospheric pressure.

Liquid fatty acid triglycerides are also particularly suitable fatty components which are liquid at 20° C.

For a $C_{12}$-$C_{30}$ fatty acid triglyceride, in the context of the present invention, the triesters of trivalent alcohol glycerol are understood with three equivalents of fatty acid. Both structurally identical and different fatty acids within a triglyceride molecule can be involved in the ester formations, the premise being that the fatty acid triglyceride has a melting point below 20° C.

According to the invention, fatty acids are to be understood as saturated or unsaturated, unbranched or branched, unsubstituted or substituted $C_{12}$-$C_{30}$ carboxylic acids. Unsaturated fatty acids may be mono-unsaturated or polyunsaturated. With an unsaturated fatty acid, the C—C double bond(s) thereof may have the cis or trans configuration.

Notable for particular suitability are fatty acid triglycerides in which at least one of the ester groups originating from glycerol is formed with a fatty acid, selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid], linolenic acid [(9Z,12Z,15Z)-octadeca-9,12,15-trienoic acid], eleostearic acid [(9Z,11E,13E)-octadeca-9,11,3-trienoic acid], arachidonic acid [(5Z,8Z,11Z,14Z)-eicosa-5,8,11,14-tetraenoic acid], and/or nervonic acid [(15Z)-tetracos-15-enoic acid].

Another particularly preferred embodiment is therefore an agent for dyeing keratin material which is characterized in that it contains, as a fatty component (c) that is liquid at 20° C., a naturally occurring fatty acid triglyceride and/or mixtures of naturally occurring fatty acid triglycerides which are contained in soybean oil, peanut oil, olive oil, sunflower oil, macadamia nut oil, moringa oil, apricot seed oil, marula oil and/or optionally hydrogenated castor oil.

Liquid fatty alcohols are also particularly suitable fatty components that are liquid at 20° C.

Preferred linear unsaturated fatty alcohols are (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), gadoleyl alcohol ((9Z)-eicos-9-en-1-ol), arachidone alcohol ((5Z,8Z,11Z,14Z)-eicosa-5,8,11,14-tetraen-1-ol), erucyl alcohol ((13Z)-docos-13-en-1-01), and/or brassidyl alcohol ((13E)-docosen-1-01). One example of a branched liquid fatty alcohol is 2-octyldodecanol.

Ester oils are also particularly suitable fatty components that are liquid at 20° C.

Ester oils are understood to be esters of $C_{12}$-$C_{30}$ fatty acids with aliphatic $C_1$-$C_{24}$ alcohols that have a liquid aggregate state at room temperature (25° C.). In other words, ester oils according to the invention are characterized in that they have a melting point at standard pressure (1013 mbar) which is below 25° C.

A particularly strong improvement in the hair feel was obtained when an post-treatment agent was applied to the previously colored hair which contained at least one ester oil from the group consisting of monoesters of $C_{12}$-$C_{24}$ fatty acids with aliphatic monovalent $C_1$-$C_{24}$ alcohols.

In the context of another very particularly preferred embodiment according to the invention, the post-treatment agent contains at least one fatty component (N-3) from the group of esters consisting of a $C_{12}$-$C_{30}$ fatty acid and an aliphatic monovalent $C_1$-$C_{24}$ alcohol.

$C_{12}$-$C_{24}$ fatty acids are very particularly suitable within the group of $C_{12}$-$C_{30}$ fatty acids. Examples of $C_{12}$-$C_{24}$ fatty acids which are suitable for forming the ester oils (N-3) are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, eleostearic acid, arachidic acid, gadoleic acid, behenic acid and erucic acid and technical mixtures thereof. Examples of the fatty alcohol components in the ester oils are isopropyl alcohol, caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, eleostearyl alcohol, arachyl alcohol, gadoleyl alcohol, behenyl alcohol, erucyl alcohol and brassidyl alcohol and technical mixtures thereof.

These $C_{12}C_{24}$ fatty acids are esterified by reaction with $C_1C_{24}$ aliphatic alcohol, which is particularly preferably a monoalcohol, so that the esterification produces a monoester.

The aliphatic $C_1C_{24}$ alcohols may be linear or branched, saturated, or mono- or polyunsaturated.

For example, an alcohol selected from the group consisting of methanol, ethanol, n-propanol, iso-propanol, n-butanol, n-pentanol, 2-ethyl-hexanol, n-hexanol, n-octanol, n-decanol and n-dodecanol can be used as the $C_1C_{24}$ aliphatic saturated alcohol.

Examples of a monovalent, unsaturated, $C_1C_{24}$ alcohol are oleyl alcohol (octadec-9-en-1-ol), palm itoleyl alcohol (cis-9-hexadecen-1-ol), elaidyl alcohol (trans-9-octadecen-1-01), and cis-11-octadecen-1-ol.

To form the esters according to the invention (N-3), the $C_{12}C_{24}$ fatty acids and the $C_1C_{12}$ alcohols are selected such that the ester formed by esterification from the two reactants is an ester oil, i.e., it has a melting point below 25° C. at 1013 mbar.

Some ester oils according to the invention can be used in the form of commercially available raw materials which are mixtures of the esters which are obtained from fatty acids of different chain length and/or alcohols of different chain lengths. These raw materials can have a melting range. With these raw materials, a melting point below 25° C. means that the melting process starts at a temperature below 25° C.

If, for example, an ester oil in the form of a specific raw material can be used in the agent, where this raw material has a melting range of 16 to 27° C., this raw material contains at least one ester oil with a melting point below 25° C. This ester oil is therefore according to the invention.

Particularly preferred according to the invention are 2-ethylhexyl palmitate (Cegesoft® 24), isopropyl myristate (Rilanit® IPM), isononanoic acid $C_{16}$-18 alkyl ester (Cetiol® SN), stearic acid 2-ethylhexyl ester (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilanit® IPP), oleyl oleate (Cetio®), lauric acid hexyl ester (Cetiol® A), di-n-butyl adipate (Cetiol® B), cetearyl isononanoate (Cetiol® SN), and oleic acid decyl ester (Cetiol® V).

Most preferably, the ester oil (N-3) is selected from the group consisting of isopropyl myristate, 2-ethylhexyl palmitate, isononanoic acid C16-18 alkyl ester, stearic acid 2-ethylhexyl ester, cetyloleate, coconut fatty alcohol caprinate, coconut fatty alcohol caprylate, n-butyl stearate, oleyl erucate, isopropyl palmitate, oleyl oleate, lauric acid hexyl ester, cetearyl isononanoate and oleic acid decyl ester.

Alternatively, isopropyl myristate is also referred to as myristic acid isopropyl ester and has the CAS number 110-27-0. Isopropyl myristate is a colorless and odorless liquid. The melting point is bsi 0-1° C.

2-ethylhexyl palmitate is alternatively also referred to as hexadecanoic acid 2-ethylhexyl ester and has the CAS number 29806-73-3. 2-ethylhexyl palmitate is a branched, saturated ester oil of palmitic acid and ethylhexyl alcohols. 2-ethylhexyl palmitate is present at room temperature in the form of a clear, colorless liquid which has a slightly greasy odor.

Isononanoic acid C16-18 alkyl ester is alternatively referred to as a cetearyl isononanoate; this ester bears the CAS numbers of 84878-33-1 and 84878-34-2. Isononanoic acid C16-18 alkyl ester is a clear, slightly yellowish liquid. At 20° C., isononanoic acid C16-18 alkyl ester has a viscosity of 19-22 mPas.

Stearic acid 2-ethylhexyl ester is alternatively also termed ethylhexyl stearate and has the CAS number 91031-48-0. Stearic acid 2-ethylhexyl ester is in the form of a clear, slightly yellowish, low-viscosity oil. At 20° C., stearic acid 2-ethylhexyl ester has a viscosity of 14-16 mPas and is accordingly an oil at room temperature.

Cetyloleate has the CAS number 22393-86-8.

Coconut fatty alcohol caprylate/caprate bears the CAS number 95912-86-0. It is a mixture of C8-C10 fatty acids with C12-C18 fatty alcohols which exists in the form of a yellow liquid and has a melting point of 10° C.

n-butyl stearate is alternatively also referred to as stearic acid butyl ester and has the CAS numbers 85408-76-0 ($C_{16}$-18) and 123-95-5 (C18). n-butyl stearate is a yellowish liquid and begins to melt starting at 16° C.

Oleyl erucate bears the CAS number 17673-56-2. Oleyl erucate is a yellow liquid. At 20° C., oleyl erucate has a viscosity of 40-50 mpas and is therefore an oil at room temperature.

Isopropyl palmitate is alternatively also referred to as propan-2-yl hexadecanoate and has the CAS number 142-91-6. The melting point of isopropyl palmitate is 13.5° C.

Alternatively, oleyl oleate is also termed cis-9,10-octadecenyl-cis-9,10-octadecanoate or oleic acid oleyl ester and has the CAS number 3687-45-4. Oleyl oleate is a clear, slightly yellowish oil which at 20° C. has a viscosity of 25-30 mPas and is an oil at room temperature.

Lauric acid hexyl ester is alternatively also referred to as hexyl laurate and has the CAS number 34316-64-8. Lauric acid hexyl ester is a clear, yellowish, odorless oil at room temperature. At 20° C., lauric acid hexyl ester has a viscosity of 5-7 mpas and is accordingly an oil at room temperature.

Cetearyl isononanoate is alternatively also referred to as isononanoic acid C16-18 alkyl ester and has the CAS numbers 84878-33-1 and 84878-34-2. Cetearyl isononanoate is a yellowish liquid with a melting point of 16-22° C.

Oleic acid decyl ester is alternatively also referred to as decyl oleate and has the CAS number 3687-46-5. Oleic acid decyl ester is a slightly yellowish liquid which has a viscosity of 15-20 mPas at 20° C. Oleic acid decyl ester is accordingly an oil at room temperature.

Preferably, the fatty component(s) (c) which are liquid at 20° C. are used in certain ranges of amounts in the agent according to the invention. Particularly good results were obtained when the agent, based on the total weight of the agent, contained one or more fatty components (c) that are liquid at 20° C. in a total amount from 1.0 to 99 wt. %, preferably from 10.0 to 90.0 wt. % and particularly preferably from 40.0 to 80.0 wt. %.

In another very particularly preferred embodiment, an agent according to the invention is characterized in that it contains, based on the total weight of the agent, one or more fatty components (c) that are liquid at 20° C. in a total amount from 1.0 to 99 wt. %, preferably from 10.0 to 90.0 wt. %, and particularly preferably from 40.0 to 80.0 wt. %.

In addition to the liquid fatty component (c) or instead of this, the agent according to the invention can also contain at least one organic solvent as component (c).

An organic solvent is understood to mean organic substances which comprise at least one carbon atom, are liquid at 20° C. and are known to a person skilled in the art in the field of chemistry as typical solvents.

Solvents within the meaning of the present invention are in particular compounds from the group of ethanol, isopropanol, 1,2-propanediol, glycerol, polyethylene glycol, phenoxyethanol and benzyl alcohol.

In the context of another very particularly preferred embodiment, an agent according to the invention is characterized in that it contains at least one solvent selected from the group consisting of ethanol, isopropanol, 1,2-propanediol, glycerol, polyethylene glycol, phenoxyethanol and benzyl alcohol.

Preferably, the solvent(s) (c) are used in certain ranges of amounts in the agent according to the invention. Particularly good results were obtained when the agent contained, based on the total weight of the agent, one or more solvents (c) in a total amount from 1.0 to 99 wt. %, preferably from 10.0 to 90.0 wt. % and particularly preferably from 40.0 to 80.0 wt. %.

In the context of another very particularly preferred embodiment, an agent according to the invention is characterized in that it contains, based on the total weight of the agent, one or more solvents (c) in a total amount from 1.0 to 99 wt. %, preferably from 10.0 to 90.0 wt. % and particularly preferably from 40.0 to 80.0 wt. %.

Application of the Agent

In the context of one embodiment, the agent according to the invention can be applied directly as such to keratin material or hair in its previously described form. In this form, the agent according to the invention also represents the ready-to-use agent.

A great advantage of this form of application is the convenient and simple form of application since the user can easily remove the agent from the bottle or the container in which it was provided and apply it to the keratin material. With this embodiment, mixing, shaking and/or homogenization with one or more further components or compositions is unnecessary. In order to ensure sufficiently high storage stability, the agent is preferably made with little or no water so that the water content of the agent, based on the total weight of the agent, is in a range from 0 to 25.0 wt. %, preferably from 0 to 10.0 wt. %, more preferably from 0 to 5.0 wt. %, and particularly preferably from 0 to 3.0 wt. %.

Within the context of another embodiment, a particularly preferred agent is characterized in that it contains, based on the total weight of the composition, from 0 to 25.0 wt. %, preferably from 0 to 10.0 wt. %, more preferably from 0 to 5.0 wt. %, and particularly preferably from 0 to 3.0 wt. %, water.

Furthermore, however, it is likewise possible to formulate the agent in the form of a concentrate and mix it with water before application. The agent provided for the user is preferably also made with little or no water. Shortly before application, the user can mix this agent with a specific amount of water. For this purpose, the user can, for example, provide the agent in a container, wherein the container is filled only to a certain extent and bears a marking on its edge which indicates the amount to which the container is to be filled with water by the user.

Further Optional Components of the Agent

In addition to the essential components (a), (b) and (c), the agent can also contain further ingredients as non-mandatory components.

The agent can also contain one or more surfactants. The term surfactants is understood to mean surface-active substances. A distinction is made between anionic surfactants consisting of a hydrophobic functional group and a negatively charged hydrophilic head group, amphoteric surfactants which bear both a negative and a compensating positive charge, cationic surfactants which have a positively charged hydrophilic group in addition to a hydrophobic functional group, and non-ionic surfactants which have no charges but strong dipole moments and are strongly hydrated in aqueous solution.

The term "zwitterionic surfactants" refers to surface-active compounds that bear at least one quaternary ammonium group and at least one —COO$^{(-)}$ or —SO$_3^{(-)}$ group in the molecule. Particularly suitable zwitterionic surfactants are the so-called betaines such as N-alkyl-N,N-dimethylammonium glycinates, for example cocoalkyl dimethylammonium glycinate, N-acylaminopropyl-N,N-dimethylammonium glycinates, for example the cocosacylaminopropyl dimethylammonium glycinate, and 2-alkyl-3-carboxymethyl-3-hydroxyethylimidazolines, each having 8 to 18 carbon atoms in the alkyl or acyl group, as well as cocosacylaminoethyl hydroxyethyl carboxymethyl glycinate. A preferred zwitterionic surfactant is the fatty acid amide derivative known under the INCI name Cocamidopropyl Betaine.

Ampholytic surfactants are understood to be surface-active compounds
which, in addition to a $C_8$-$C_{24}$ alkyl or acyl group, also contain at least one free amino group and at least one —COOH— or —SO$_3$H group in the molecule and are capable of forming inner salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 24 carbon atoms in the alkyl group. Typical examples of amphoteric or zwitterionic surfactants are alkyl betaines, alkylamidobetaines, amino propionate, aminoglycinates, imidazolinium betaines and sulfobetaines.

Particularly preferred ampholytic surfactants are N-cocoalkyl aminopropionate, cocoacylaminoethyl aminopropionate, and $C_{12}$-$C_{18}$ acyl sarcosine.

The agents can also contain at least one non-ionic surfactant. Suitable non-ionic surfactants are alkyl polyglycosides and alkylene oxide adducts to fatty alcohols and fatty acids with in each case 2 to 30 mol of ethylene oxide per mole of fatty alcohol or fatty acid. Preparations with good properties are likewise obtained when they contain fatty acid esters of ethoxylated glycerin as non-ionic surfactants which have been reacted with at least 2 mol ethylene oxide. The non-ionic surfactants are used in a total amount from 0.1 to 45 wt. %, preferably 1 to 30 wt. %, and very particularly preferably from 1 to 15 wt. %, based on the total weight of each agent.

Furthermore, the agents can additionally also contain at least one cationic surfactant. Cationic surfactants are understood to mean surfactants, i.e. surface-active compounds, each having one or more positive charges. Cationic surfactants contain exclusively positive charges. Typically, these surfactants are composed of a hydrophobic part and a hydrophilic head group, with the hydrophobic part generally consisting of a hydrocarbon framework (e. g., consisting of one or two linear or branched alkyl chains), and the positive charge(s) being located in the hydrophilic head group. Examples of cationic surfactants are:
quaternary ammonium compounds which can carry one or two alkyl chains having a chain length of 8 to 28 C atoms as hydrophobic functional groups,
quaternary phosphonium salts substituted with one or more alkyl chains having a chain length of 8 to 28 C atoms, or
tertiary sulfonium salts.

Furthermore, the cationic charge can also be part of a heterocyclic ring (for example an imidazolium ring or a pyridinium ring) in the form of an onium structure. In addition to the functional unit carrying the cationic charge, the cationic surfactant can also contain further uncharged functional groups, as is the case, for example, with esterquats. The cationic surfactants are used in a total amount from 0.1 to 45 wt. %, preferably 1 to 30 wt. %, and very particularly preferably from 1 to 15 wt. %, based on the total weight of each agent.

Furthermore, the agents according to the invention can also contain at least one anionic surfactant. Anionic surfactants are surface-active agents with exclusively anionic charges (neutralized by a corresponding counter cation). Examples of anionic surfactants are fatty acids, alkyl sulfates, alkyl ether sulfates, and ether carboxylic acids having 12 to 20 C atoms in the alkyl group and up to 16 glycol ether groups in the molecule.

The anionic surfactants are used in a total amount from 0.1 to 45 wt. %, preferably 1 to 30 wt. %, and very particularly preferably from 1 to 15 wt. %, based on the total weight of each agent.

If the agent contains water or is to be mixed with water before the application, the agent for setting the desired pH can then also contain at least one alkalizing agent and/or acidifying agent. The pH values within the meaning of the present invention are pH values which have been measured at a temperature of 22° C.

Agents (a), (b) and (c) may contain, for example, ammonia, alkanolamines and/or basic amino acids as alkalizing agents.

The alkanolamines that can be used as alkalizing agents of the invention are preferably selected from primary amines having a $C_2$-$C_6$ alkyl parent substance, which carries at least one hydroxyl group. Preferred alkanolamines are selected from the group which is formed of 2-aminoethan-1-ol (monoethanolamine), 3-aminopropan-1-ol, 4-aminobutan-1-ol, 5-amino-pentan-1-ol, 1-aminopropan -2-ol, 1-aminobutan-2-ol, 1-amino-pentan-2-ol, 1-amino-pentan-3-ol, 1-amino-pentan-4-ol, 3-amino-2-methylpropan-1-ol, 1-amino-2-methylpropan-2-ol, 3-aminopropane-1,2-diol and 2-amino-2-methyl propane-1,3-diol.

Alkanolamines particularly preferred according to the invention are selected from 2-aminoethan-1-ol and/or 2-amino-2-methylpropan-1-ol. A particularly preferred embodiment is therefore characterized in that the agent according to the invention contains, as an alkalizing agent, an alkanolamine selected from 2-aminoethan-1-ol and/or 2-amino-2-methylpropan-1-ol.

An amino acid within the meaning of the invention is an organic compound which contains at least one protonatable amino group and at least one —COOH or one —SO$_3$H group in its structure. Preferred amino acids are aminocarboxylic acids, in particular α-(alpha)-amino-carboxylic acids and ω-aminocarboxylic acids, with α-aminocarboxylic acids being particularly preferred.

According to the invention, basic amino acids are understood to mean the amino acids which have an isoelectric point pI greater than 7.0.

Basic α-aminocarboxylic acids contain at least one asymmetric carbon atom. In the context of the present invention, both possible enantiomers can equally be used as a specific compound or else mixtures thereof, in particular as racemates. However, it is particularly advantageous to use the naturally occurring isomer form, usually in the L configuration.

The basic amino acids are preferably selected from the group, which is formed of arginine, lysine, ornithine and histidine, more preferably of arginine and lysine. In another particularly preferred embodiment, an agent according to the invention is therefore characterized in that the alkalizing agent is a basic amino acid from the group of arginine, lysine, ornithine and/or histidine.

Furthermore, the agent can contain additional alkalizing agents, in particular inorganic alkalizing agents. According to the invention, usable, inorganic alkalizing agents are preferably selected from the group, which is formed of sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Very particularly preferred alkalizing agents are ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Acidifying agents familiar to a person skilled in the art are, for example, edible acids such as citric acid, acetic acid, maleic acid or tartaric acid, and dilute mineral acids such as hydrochloric acid, sulfuric acid or phosphoric acid.

The agents can also contain other active ingredients, auxiliaries and additives, such as thickening polymers, film-forming polymers, structurants such as glucose, maleic acid and lactic acid, hair-conditioning compounds such as phospholipids, for example lecithin and cephalins; perfume oils, dimethyl isosorbide and cyclodextrins; fiber structure-improving agents, in particular mono-, di- and oligosaccharides, for example glucose, galactose, fructose and lactose; dyes for coloring the product; anti-dandruff active ingredients such as piroctone olamine, zinc omadine and climbazole; amino acids and oligopeptides; animal and/or vegetable-based protein hydrolysates, as well as in the form of their fatty acid condensation products or optionally anionically or cationically modified derivatives; light stabilizers and UV blockers; active ingredients such as panthenol, pantothenic acid, pantolactone, allantoin, pyrrolidinone carboxylic acids and their salts, and bisabolol; polyphenols, in particular hydroxycinnamic acids, 6,7-dihydroxycoumarins, hydroxybenzoic acids, catechins, tannins, leucoanthocyanidins, anthocyanidins, flavanones, flavones and flavonols; ceramides or pseudoceramides; vitamins, provitamins and vitamin precursors; plant extracts; fats and waxes such as fatty alcohols, beeswax, montan wax and kerosenes; swelling and penetrating agents such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate as well as PEG-3-distearate; and propellants such as propane-butane mixtures, $N_2O$, dimethyl ether, $CO_2$ and air.

Very particularly preferably, the agent (b) contains at least one anionic polymer from the group of copolymers of acrylic acid, the copolymers of methacrylic acid, the homopolymers or copolymers of acrylic acid esters, the homopolymers or copolymers of methacrylic acid esters, the homopolymers or copolymers of acrylic acid amides, the homopolymers or copolymers of methacrylic acid amides, the copolymers of vinylpyrrolidone, the copolymers of vinyl alcohol, the copolymers of vinyl acetate, the homopolymers or copolymers of ethylene, the homopolymers or copolymers of propylene, the homopolymers or copolymers of styrene, the polyurethanes, the polyesters and/or the polyamides.

The selection of these additional substances is made by the skilled artisan according to the desired properties of the agents. In regard to other facultative components and the employed amounts of said components, reference is made expressly to relevant handbooks known to the skilled artisan. The additional active ingredients and auxiliaries are used in the preparations according the invention preferably in each case in amounts from 0.0001 to 25 wt. %, in particular from 0.0005 to 15 wt. %, based on the total weight of the particular agent.

Method for Dyeing Keratin Materials

The agent according to the invention is applied to the keratin materials, in particular to human hair, and is therefore particularly suitable for use in a process for dyeing keratin material. Very particularly preferably, the agent of the first object of the invention is used in agents for dyeing hair.

The present invention therefore also relates to a method for dyeing human hair, comprising the following steps in the indicated order:
  (1) moistening the hair with water,
  (2) applying an agent as disclosed in detail in the description of the first object of the invention to the moistened hair,
  (3) allowing the agent to act for a period from 10 seconds to 30 minutes, preferably from 10 seconds to 15 minutes, and
  (4) rinsing out the hair with water.

In the first step, the hair is dampened or moistened with water. This can be done by wetting the hair only with water, or else the hair is washed with the aid of a shampoo, the shampoo is rinsed out, and then the agent according to the invention is applied to the still moist hair.

The agent is applied in step (2), wherein the agent according to the invention can directly be the agent, preferably with little to no water, which was described in the description of the first subject of the invention. In this case, the hydrolysis and the condensation of the silanes initiated by the hydrolysis occur due to the moisture present in the hair.

As already described above, however, the agent according to the invention is also mixed with water before application. In this case, the dyeing method according to the invention comprises mixing the agent with water as an additional step.

In the context of this embodiment, a method for dyeing human hair is preferred, comprising the following steps in the indicated order:
  (1) moistening the hair with water,
  (2) providing an agent as was disclosed in detail in the description of the first object of the invention, and mixing the agent with water,
  (3) applying the ready-to-use agent prepared in step (2) to the moistened hair,
  (4) allowing the agent applied in step (3) to act for a period from 10 seconds to 30 minutes, preferably from 10 seconds to 15 minutes, and
  (5) rinsing out the hair with water.

The agent can be applied to the hair for example with the aid of a small brush, a brush or a nozzle, or the user can use their gloved hand for this purpose.

In step (3), or when the agent is mixed with water beforehand in step (4), the agent previously applied to the hair is allowed to act on the hair for a period from 10 seconds to 30 minutes, preferably from 10 seconds to 15 minutes. The action can be assisted by heat. Also, the user or hairdresser can massage the product into the hair while it is acting.

In step (4) or in step (5), the agent is then rinsed out of the hair. Rinsing can be carried out with water, or the hair is rinsed with water with the aid of a shampoo and/or a conditioner.

Concerning the additional preferred embodiments of the method according to the invention, what has been said about the agent according to the invention applies mutatis mutandis.

The invention claimed is:

1. An agent for dyeing keratin material, the agent comprising:
   at least two organosilicon compounds, wherein each organosilicon compound is a silane with one, two, or three silicon atoms that comprises one or more hydroxyl groups and/or hydrolyzable groups per molecule;
   at least one pigment;
   at least one fatty component that is a liquid at 20° C. and/or an organic solvent; and
   water in an amount ranging from 0 to 25.0 wt. %, based on the total weight of the agent.

2. The agent of claim 1, wherein the at least two organosilicon compounds comprise at least one first organosilicon compound of formula (I) and/or (II):

$R_1R_2N-L-Si(OR_3)_a(R_4)_b$     (I)

wherein:
   $R_1$ and $R_2$ are each, independently, a hydrogen atom or a $C_1$-$C_6$ alkyl group,
   L is a linear or branched divalent $C_1$-$C_{20}$ alkylene group,
   $R_3$ and $R_4$ are each, independently, a $C_1$-$C_6$ alkyl group,
   a is 1, 2 or 3, and
   b is 3-a, and $(R_5O)_c(R_6)_dSi-(A)_e-[NR_7-(A')]_f-[O-(A'')]_g-[NR_8-(A''')]_h-Si(R_6')_{d'}(OR_5')_{c'}$     (II)

wherein:
   $R_5$, $R_5'$, $R_5''$, $R_6$, $R_6'$ and $R_6''$ represent are each, independently, of one another, a $C_1$-$C_6$ alkyl group,
   A, A', A'', A''' and A'''' are each, independently, a linear or branched, divalent $C_1$-$C_{20}$ alkylene group,
   $R_7$ and $R_8$ are each, independently, a hydrogen atom, a $C_1$-$C_6$ alkyl group, a hydroxy $C_1$-$C_6$ alkyl group, a $C_2$-$C_6$ alkenyl group, an amino $C_1$-$C_6$ alkyl group, or a group of formula (III):

$(A'''')-Si(R_6'')_{d''}(OR_5'')_{c''}$     (III)

wherein:
   c is 1, 2 or 3,
   d is 3-c,
   c' is 1, 2 or 3,
   d' is 3-c',
   c'' is 1, 2 or 3,
   d'' is 3-c',
   e is 0 or 1,
   f is 0 or 1,
   g is 0 or 1, and
   h is 0 or 1,
   with the proviso that at least one of e, f, g and h is not 0.

3. The agent of claim 2, wherein the at least one first organosilicon compound of formula (I) is represented by:

$R_1R_2N-L-Si(OR_3)_a(R_4)_b$     (I)

wherein:
   $R_1$ and $R_2$ are both hydrogen atom,
   L is a linear, divalent $C_1$-$C_6$ alkylene group,
   $R_3$ and $R_4$ are each, independently, a methyl group or an ethyl group,
   a is 3, and
   b is 0.

4. The agent of claim 2, wherein the at least one first organosilicon compound of formula (I) is selected from the group consisting of:
   (3-aminopropyl) trimethoxysilane,
   (3-aminopropyl)triethoxysilane,
   (2-aminoethyl)trimethoxysilane,
   (2-aminoethyl)triethoxysilane,
   (3-dimethylaminopropyl) trimethoxysilane,
   (3-dimethylaminopropyl)triethoxysilane,
   (2-dimethylaminoethyl)trimethoxysilane,
   (2-dimethylaminoethyl)triethoxysilane, and
   any combination thereof.

5. The agent of claim 2, wherein the at least one first organosilicon compound of formula (II) is represented by:

$(R_5O)_c(R_6)_dSi-(A)_e-[NR_7-(A')]_f-[O-(A'')]_g-[NR_8-(A''')]_h-Si(R_6')_{d'}(OR_5')_{c'}$     (II)

wherein:
   e and f are both 1,
   g and h are both 0,
   A and A' are each, independently, a linear, divalent $C_1$-$C_6$ alkylene group, and
   $R_7$ represents $R_7$ is a hydrogen atom, a methyl group, a 2-hydroxyethyl group, a 2-alkenyl group, a 2-aminoethyl group, or a group of formula (III).

6. The agent of claim 2, wherein the at least one first organosilicon compound of formula (II) is selected from the group consisting of:
   3-(trimethoxysilyl)-N-[3-(trimethoxysilyl) propyl]-1-propanamine,
   3-(triethoxysilyl)-N-[3-(triethoxysilyl) propyl]-1-propanamine,
   N-methyl-3-(trimethoxysilyl)-N-[3-(trimethoxysilyl) propyl]-1-propanamine,
   N-methyl-3-(triethoxysilyl)-N-[3-(triethoxysilyl) propyl]-1-propanamine,
   2-[bis [3-(trimethoxysilyl) propyl]amino]ethanol,
   2-[bis [3-(triethoxysilyl) propyl]amino]ethanol,
   3-(trimethoxysilyl)-N,N-bis [3-(trimethoxysilyl) propyl]-1-propanamine,
   3-(triethoxysilyl)-N,N-bis [3-(triethoxysilyl) propyl]-1-propanamine,
   N1,N1-bis [3-(trimethoxysilyl) propyl]-1,2-ethanediamine,
   N1,N1-bis [3-(triethoxysilyl) propyl]-1,2-ethanediamine,
   N,N-bis [3-(trimethoxysilyl) propyl]-2-propen-1-amine,
   N,N-bis [3-(triethoxysilyl) propyl]-2-propen-1-amine, and
   any combination thereof.

7. The agent to of claim 1, wherein the at least two organosilicon compounds comprise at least one second organosilicon compound of formula (IV):

$R_9Si(OR_{10})_k(R_{11})_m$     (IV)

wherein:
R$_9$ is a C$_1$-C$_{12}$ alkyl group,
R$_{10}$ is a hydrogen atom or a C$_1$-C$_6$ alkyl group,
R$_{11}$ is a C$_1$-C$_6$ alkyl group,
k is 1, 2 or 3, and
m is 3-k.

8. The agent of claim 7, wherein the at least one second organosilicon compound of formula (IV) is selected from the group consisting of:
methyltrimethoxysilane,
methyltriethoxysilane,
ethyltrimethoxysilane,
ethyltriethoxysilane,
hexyltrimethoxysilane,
hexyltriethoxysilane,
octyltrimethoxysilane,
octyltriethoxysilane,
dodecyltrimethoxysilane,
dodecyltriethoxysilane, and
combinations any combination thereof.

9. The agent of claim 2, wherein the at least one first organosilicon compound is present in an amount ranging from 0.1 to 99.0 wt. %, based on the total weight of the agent.

10. The agent to of claim 7, wherein the at least one second organosilicon compound is present in an amount ranging from 0.1 to 99.0 wt. %, based on the total weight of the agent.

11. The agent of claim 1, wherein the at least one pigment is selected from the group consisting of colored metal oxides, metal hydroxides, metal oxide hydrates, silicates, metal sulfides, complex metal cyanides, metal sulphates, bronze pigments, mica-based colored pigments coated with at least one metal oxide, metal oxychloride oxychlorides, and any combination thereof.

12. The agent of claim 1, wherein the at least one pigment is selected from the group consisting of carmine, quinacridone, phthalocyanine, sorghum, blue pigments with the Color Index numbers CI 42090, CI 69800, CI 69825, CI 73000, CI 74100, or CI 74160, yellow pigments with the Color Index numbers CI 11680, CI 11710, CI 15985, CI 19140, CI 20040, CI 21100, CI 21108, CI 47000, or CI 47005, green pigments with the Color Index numbers CI 61565, CI 61570, or CI 74260, orange pigments with the Color Index numbers CI 11725, CI 15510, CI 45370, or CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470, and any combination thereof.

13. The agent of claim 1, wherein the at least one pigment is present in an amount ranging from 1.0 to 20.0 wt. %, based on the total weight of the agent.

14. The agent of claim 1, wherein the at least one fatty component is selected from the group consisting of linear silicone oils, cyclic silicone oils, hydrocarbon oils, liquid fatty acid triglycerides, liquid fatty alcohols, ester oils, and any combination thereof.

15. The agent of claim 1, wherein the at least one fatty component comprises at least one silicone oil of formula (V) and/or (VI):

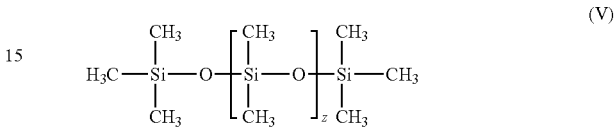

wherein z is an integer from 0 to 10,000,

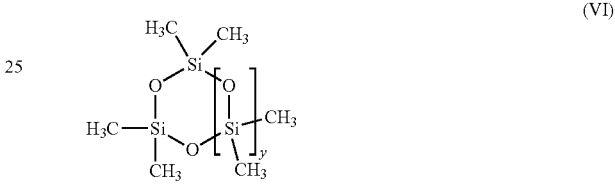

wherein y is 1, 2, 3, 4 or 5.

16. The agent according to of claim 1, wherein the at least one fatty component is present in an amount ranging from 1.0 to 99 wt. %, based on the total weight of the agent.

17. The agent of claim 1, further comprising at least one solvent selected from the group consisting of ethanol, isopropanol, 1,2-propanediol, glycerol, polyethylene glycol, phenoxyethanol, benzyl alcohol, and any combination thereof.

18. The agent of claim 17, wherein the at least one solvent is present in an amount ranging from 1.0 to 99 wt. %, based on the total weight of the agent.

19. A method for dyeing keratin material, the method comprising:
moistening the keratin material with water;
applying the agent of claim 1 to the moistened hair;
maintaining the agent in contact with the moistened hair for an amount of time ranging from 10 seconds to 30 minutes; and
rinsing the agent from the moistened hair with water.

* * * * *

UNITED STATES PATENT AND TRADEMARK OFFICE
CERTIFICATE OF CORRECTION

PATENT NO. : 12,329,840 B2
APPLICATION NO. : 18/272368
DATED : June 17, 2025
INVENTOR(S) : Phillip Jaiser et al.

It is certified that error appears in the above-identified patent and that said Letters Patent is hereby corrected as shown below:

In the Specification

Column 8, Line 61 change "(A'-)" to --(A'''-)--.
Column 9, Line 17 change "$(R_5O)\ _c(R_6)\ _d\ Si-(A)\ _e-[NR_7-(A')]_f-[O-(A'')]_g-[NR_8-(A''')]_n-Si(R_6')_{d'}(OR_5')_{c'}$" to --$(R_5O)_c(R_6)_{d'}Si-(A)_e-[NR_7-(A')]_f-[O-(A'')]_g-[NR_8-(A''')]_h-Si(R_6')_{d'}(OR_5')_{c'}$--.
Column 14, Line 19 change "Ru" to --R11--.
Column 14, Line 21 change "Ru" to --R11--.

Signed and Sealed this
Second Day of December, 2025

John A. Squires
*Director of the United States Patent and Trademark Office*